US006765092B2

(12) United States Patent
Lindsey et al.

(10) Patent No.: US 6,765,092 B2
(45) Date of Patent: Jul. 20, 2004

(54) REGIOISOMERICALLY PURE OXOCHLORINS AND METHODS OF SYNTHESIS

(75) Inventors: Jonathan S. Lindsey, Raleigh, NC (US); Masahiko Taniguchi, Raleigh, NC (US); Sreedharan Prathapan, Kerala (IN); Man Nyoung Kim, Daejeon (KR); Han-Je Kim, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 231 days.

(21) Appl. No.: 10/011,121

(22) Filed: Dec. 7, 2001

(65) Prior Publication Data

US 2002/0137925 A1 Sep. 26, 2002

Related U.S. Application Data

(63) Continuation-in-part of application No. 09/852,560, filed on May 10, 2001, now Pat. No. 6,559,374, which is a continuation-in-part of application No. 09/670,463, filed on Sep. 26, 2000, now abandoned, which is a continuation-in-part of application No. 09/621,797, filed on Jul. 21, 2000, now Pat. No. 6,420,648.

(51) Int. Cl.[7] ............................................. C07D 487/22

(52) U.S. Cl. ....................................................... 540/145

(58) Field of Search ......................................... 540/145

(56) References Cited

U.S. PATENT DOCUMENTS

| | | | | |
|---|---|---|---|---|
| 4,618,509 A | 10/1986 | Bulkowski | .................... | 427/74 |
| 5,004,811 A | 4/1991 | Bommer et al. | ............. | 540/145 |
| 5,064,952 A | 11/1991 | Chang et al. | ................ | 540/149 |
| 5,093,349 A | 3/1992 | Pandey et al. | ............... | 514/410 |
| 5,145,863 A | 9/1992 | Dougherty et al. | ............ | 514/10 |
| 5,241,062 A | 8/1993 | Wijesekera et al. | .......... | 540/145 |
| 5,280,183 A | 1/1994 | Batzel et al. | ................. | 257/40 |
| 5,330,741 A | 7/1994 | Smith et al. | ................. | 514/410 |
| 5,371,199 A | 12/1994 | Therien et al. | .............. | 534/140 |
| 5,424,974 A | 6/1995 | Liu et al. | ..................... | 365/112 |
| 5,441,827 A | 8/1995 | Gratzel et al. | ............... | 429/111 |
| 6,212,093 B1 | 4/2001 | Lindsey | ........................ | 365/151 |
| 6,232,547 B1 | 5/2001 | Meissner et al. | ............ | 136/253 |

FOREIGN PATENT DOCUMENTS

| | | |
|---|---|---|
| EP | 0 780 391 A2 | 6/1997 |
| WO | WO 98/50393 | 11/1998 |
| WO | WO 00/11725 | 3/2000 |
| WO | WO 02/092601 | 11/2002 |

OTHER PUBLICATIONS

Albery, W. John; *Development of Photogalvanic Cells for Solar Energy Conversion* Acc. Chem. Res., 15:142–148 (1982).

Bach et al.; *Solid–State Dye–Sensitized Mesoporous TiO₂ Solar Cells with High Photon–to–Electron Conversion Efficiencies*, Nature395:583–585 (Oct. 1998).

Balasubramanian, Thiagarajan, et al., *Rational Synthesis of β–Substituted Chlorin Building Blocks*, J. Org. Chem., vol. 65, pp. 7919–7929 (2000).

Brune, Daniel C., et al., *Some Newly Observed Correlations Between Structure and Photochemical Activity in Chlorophyllin a and Several Derivatives*, Acrchives of Biochemistry and Biophysics, vol. 163, pp. 552–560 (1974).

Cho, Won–Seob, et al., *Rational Synthesis of Trans–Substituted Porphyrin Building Blocks Containing One Sulfur or Oxygen Atom in Place of Nitrogen at a Designated Site*, The Journal of Organic Chemistry, vol. 64, No. 21, pp. 7890–7901 (1999).

Geier, III, G. Richard, et al., *A Survey of Acid Caqtalysts for Use in Two–Step, One–Flask Syntheses of Meso–Substituted Porphyrinic Macrocycles*, Organic Letters, vol. 2, No. 12, pp. 1745–1748 (2000).

Kamogawa, Kiroyoshi, *Preparation of Chlorophyll Polymer*, Polymer Letters, vol. 10, pp. 711–713 (1972.

Kuciauskas et al.; *An Artificial Photosynthetic Antenna–Reaction Center Complex*, J. Am. Chem. Soc., 121(37):8604–8614 (1999).

Lee, Chang–Hee, et al., *Synthetic Approaches to Regioisomerically Pure Porphyrins Bearing Four Different Meso–Substituents*, Tetrahedron, vol. 51, No. 43, pp. 11645–11672 (1995).

Li et al.; *Efficient Synthesis of Light–Harvesting Arrays Composed of Eight Porphyrins and One Phthalocyanine*, J. of Org. Chem., 64(25):9101–9108 (1999).

Littler, Benjamin J., et al., *Investigation of Conditions Giving Minimal Scrambling in the Synthesis of trans–Porphyrins from Dipyrromethanes and Aldehydes*, The Journals of Organi Chemistry, vol. 64, No. 8, pp. 2864–2872 (1999).

Moss et al.; *Sensitization of Nanocrystalline TiO₂ by Electropolymerized Thin Films*, Chem Mater., 10(7):1748–1750 (1998).

O'Regan et al.; *A Low–Cost, High–Efficiency Solar Cell Based on Dye–Sensitized Colloidal TiO₂ Films*, Nature, 353:737–739 (Oct. 1991).

Parkinson et al.; *Recent Advances In High Quantum Yield Dye Sensitization of Semiconductor Electrodes*, Electrochimica Acta., 37(5):943–948 (1992).

(List continued on next page.)

*Primary Examiner*—Richard L. Raymond
(74) *Attorney, Agent, or Firm*—Myers Bigel Sibley & Sajovec

(57) ABSTRACT

A method of making an oxochlorin comprises the steps of oxidizing a chlorin to produce a mixture of hydroxychlorin and oxochlorin, and then oxidizing the hydroxychlorin in said mixture, preferably with DDQ, to produce a mixture consisting essentially of oxochlorin. The step of oxidizing a chlorin is carried out by exposing the chlorin to alumina, typically in the presence of an oxidizing agent such as air or alumina. The oxidizing steps may be carried out in an organic solvent such as toluene. The chlorin is preferably a C-methylated chlorin, and is preferably metalated.

22 Claims, 4 Drawing Sheets

OTHER PUBLICATIONS

Rao, Polisetti Dharma, et al., *Rational Syntheses of Porphyrins Bearing up to Four Different Meso Substituents*, The Journal of Organic Chemistry, vol. 65, No. 22, pp. 7323–7344 (2000).

Schon et al.; *Efficient Organic Photovoltaic Diodes Based on Doped Pentacene*, Nature, 403:408–410 (Jan. 27, 2000).

Strachan et al.; *Rational Synthesis of Meso–Substituted Chlorin Building Blocks*, J. of Org. Chem., 65(10):3160–3172 (2000).

Wagner et al.; *A Molecular Photonic Wire*, J. Am. Chem. Soc., 116:9759–9760 (1994).

Wagner et al.; *Soluble Synthetic Multiporphyrin Arrays. 1. Modular Design and Synthesis*, J. Am. Chem. Soc., 118(45):11166–11180 (1996).

Osuka, Atsuhiro, et al., *Sequential Electron Transfer Leading to Long–Lived Charge Separated State in a Porphyrin–Oxochlorin–Pyromellitdimide Triad*, Bull. Chem. Soc. Jpn., vol. 68, pp. 262–276 (1995).

Osuka, Atsuhiro, et al., *A Stepwise Electron–Transfer Relay Mimicking the Primary Charge Separation in Bacterial Photosynthetic Reaction Center*, J. Am. Chem. Soc., vol. 118, pp. 155–168 (1996).

Barasch, Dinorah, et al., *Novel DMPO–Derived $^{13}$C–Labeled Spin Traps Yield Identifiable Stable Nitroxides*, J. Am. Chem. Soc., vol. 116, pp. 7319–7324 (1994).

Battersby, Alan R., et al., *Synthetic Studies Relevant to Biosynthetic Research on Vitamin $b_{12}$. Part 1. Syntheses of C–Methylated Chlorins Based on 1–Pyrrolines (3,4–Dihydropyrroles).*, J. Chem. Soc. Perkins Trans. I, pp. 2725–2732 (1984).

Battersby, Alan R., et al., *Synthetic Studeis Relevant to Biosynthetic Research on Vitamin $B_{12}$. Part 7. Synthesis of (±)–Bonellin Dimethyl Ester*, J. Chem. Soc. Perkin Trans. I, pp. 1569–1576 (1988).

Black, David St.C., et al., *Nitrones and Oxaziridines. XXXIX Conversion of 1–Pyrroline 1–Oxides into 2H–Pyrroles through the Hetero–Cope Rearrangement*, Aust. J. Chem., vol. 42, pp. 71–78 (1989).

Janzen, Edward G., et al., *Synthesis and Spin–Trapping Chemistry of 5,5–Dimethyl–2–(trifluoromethyl)–1–pyrroline N–Oxide*, J. Org. Chem., vol. 60, pp. 5434–5440 (1995).

Krattinger, Bénédicte, et al., *Addition of Sterically hindered Organolithium Compounds to meso–Tetraphenyloporphyrin*, Tetrahedron Letters, vol. 39, pp. 1165–1168 (1998).

Lin, Jack J., et al., *Metal–Catalyzed Oxidative Cyclizations of a,c–Biladiene Salts Bearing 1–and/or 19–Arylmethyl Substituents: Macrocyclic Products and Their Chemistry*, J. Org. Chem., vol. 62, pp. 4266–4276 (1997).

Montforts, Franz–Peter, et al., *Discovery and Synthesis of Less Common Natural Hydroporphyrins*, Chem. Rev., vol. 94, pp. 327–347 (1994).

Silva, Anna M.G., et al., *Porphyrins in 1,3–depolar cycloaddition reaction with sugar nitrones. Synthesis of glycoconjugated isoxazolidine–fused chlorines and bacteriochlorins*, Tetrahedron Letters, vol. 43, pp. 603–605 (2002).

Tiecco, Marcello, et al., *Ring–closure Reaction of Alkenyl Oximes Induced by Persulfate Anion Oxidation of Diphenyl Diselenide. Formation of 1,2–Oxazines and Cyclic Nitrones*, J. Chem. Soc. Perkin Trans. I., pp. 1989–1993 (1993).

Tipton, Adrianne K, et al., *Synthesis and Metabolism of the First Thia–Bilirubin*, J. Org. Chem., vol. 66, pp. 1832–1838 (2001).

Xue, Tianhan, et al., *Bilane Synthesis through Bilene–a: An Alternative Approach*, Tetrahedron Letters, vol. 39, pp. 6651–6654 (1998).

Fungo, Fernanda, et al., *Synthesis of porphyrin dyads with potential use in solar energy conversion*, Journal of Materials Chemistry, vol. 10, pp. 645–650 (2000).

International Search Report, International Application No. PCT/US01/23010, 2001.

Gryko, et al., *Rational Synthesis of Meso–Substituted Porphyrins Bearing One Nitrogen Heterocyclic Group*, J. Org. Chem., vol. 65, pp. 2249–2252 (2000).

Taniguchi, Shozo, et al., *A Facile Route to Tripyrrane from 2,5–Bix(hydroxymethyl)Pyrrole and the Improved Synthesis of Porphine by the "3+1" Approach*, Synnlett, vol. 1, pp. 73–74 (1999).

Wallace, David M., et al., *Stepwise Syntheses of Unsymmetrical Tetra–Arylporphyrins, Adaption of the MacDonald Dipyrrole Self–Condensation Methodology*, Tet. Let., vol. 31, No. 50, pp. 7265–7268 (1990).

International Search Report for International Application No. PCT/US02/29783 dated Jul. 21, 2003.

$a_2$

US 6,765,092 B2

REGIOISOMERICALLY PURE OXOCHLORINS AND METHODS OF SYNTHESIS

RELATED APPLICATIONS

This application is a continuation in part of commonly owned, application Ser. No. 09/852,560, filed May 10, 2001, now U.S. Pat. No. 6,559,374 which is a continuation in part of commonly owned, application Ser. No. 09/670,463, filed Sep. 26, 2000, now abandoned which is a continuation in part of Ser. No. 09/621,797, filed Jul. 21, 2000, now U.S. Pat. No. 6,420,648 the disclosures of all of which are incorporated by reference herein in their entirety.

FIELD OF THE INVENTION

The present invention concerns oxochlorin compounds, methods of making the same, and polymers, light harvesting arrays, and solar cells formed therefrom.

BACKGROUND OF THE INVENTION

The synthesis of light-harvesting rods can be achieved through use of porphyrinic building blocks. A major goal in the development of porphyrin or chlorin building blocks for application in light-harvesting systems is to fine-tune their photophysical and electrochemical properties. Tuning has been achieved with porphyrins by incorporating various substituents at the meso as well as β-positions, introduction of different core metals, etc. (Li, F. et al., *J. Mater. Chem.* 1997, 7, 1245–1262; Yang, S. I. et al., *J. Porphyrins Phthalocyanines* 1999, 3, 117–147; Yang, S. I. et al., *J. Am. Chem. Soc.* 1999, 121, 4008–4018). Chlorins have two considerable advantages for light-harvesting applications in comparison with porphyrins: (1) the extinction coefficient of the long-wavelength absorption band is greater than that of porphyrins (Chang, C. K. et al., *Proc. Natl. Acad. Sci. USA*, 1981, 78, 2652–2656; Stolzenberg, A. M. et al., *J. Am. Chem. Soc.* 1981, 103, 4763–4778), and (2) chlorins are linear oscillators whereas metalloporphyrins are planar oscillators. These differences make chlorins superior to porphyrins for use in photosynthetic systems. Chlorin building blocks are quite attractive for applications in light-harvesting systems. The important photochemical properties of chlorins have motivated the development of a number of new syntheses of these green pigments in the past few years (Taniguchi, M. et al., *J. Org. Chem.* 2001, 66, 7342–7354; Jacobi, P. A. et al., *Org. Lett.* 2001, 3, 831–834; Montforts, F.-P. et al., *Angew. Chem. Int. Ed.* 2000, 39, 599–601; Shea, K. M. et al., *Tetrahedron.* 2000, 56, 3139–3144; Burns, D. H. et al., *Chem. Commun.* 2000, 299–300; Strachan, J.-P. et al., *J. Org. Chem.* 2000, 65, 3160–3172; Balasubramanian, T. et al., *J. Org. Chem.* 2000, 65, 7919–7929; Krattinger, B. et al., *J. Org. Chem.* 1999, 1857–1867; Johnson, C. K. et al., *Tetrahedron Lett.* 1998, 39, 4619–4622; Mironov, A. F. et al., *J. Chem. Soc. Perkin Trans.* 1 1998, 3601–3608).

Chlorin dyads are of particular interest as benchmarks for assessing the extent of electronic communication and the rates and efficiency of energy transfer between chlorins. Nevertheless, relatively little attention had been paid to the synthesis and comparative studies of covalently linked chlorin dyads, because chlorins have limited stability and the synthesis of chlorin building blocks has been quite challenging. A number of chlorin dyads with various linkages and configurations have been prepared. These chlorin dyads are categorized in the following groups: (1) chlorins with electron acceptors for electron-transfer studies (Tkachenko, N. V. et al., *J. Am. Chem. Soc.* 1999, 121, 9378–9387; Malinen, P. K. et al., *Liebigs Ann.* 1997, 1801–1804; Abel, Y. et al., *Tetrahedron Lett.* 1997, 38, 1745–1748; Zheng, G. et al., *Chem. Commun.* 1999, 2469–2470; Lindsey, J. S. et al., *J. Am. Chem. Soc.* 1988, 110, 3610–3621), (2) chlorins possessing fused aromatic rings (Kozyrev, A. N. et al., *Tetrahedron* 2000, 56, 3353–3364; Silva, A. M. G. et al., *Tetrahedron Lett.* 2000, 41, 3065–3068; Johnson, C. K. et al., *Tetrahedron Lett.* 1998, 39, 4753–4756; Krattinger, B. et al., *Chem. Commun.* 1998, 757–756), (3) chlorin-porphyrin dyads for energy-transfer studies (Faustino, M. A. et al., *Photochem. Photobiol.* 2000, 72, 217–225; Zheng, G. et al., *Tetrahedron Lett.* 1997, 38, 2409–2412; Wasielewski, M. R. et al., *Solar Energy Materials and Solar Cells* 1995, 38, 127–134; Johnson, D. G. et al., *J. Am. Chem. Soc.* 1993, 115, 5692–5701; Zenkevich, E. I. et al., *J. Luminescence* 1997, 75, 229–244), (4) chlorins with accessory pigments (Kutzki, O. et al., *Helv. Chim. Acta,* 2000, 83, 2231–2245; Wedel, M. et al., *J. Org. Chem.* 2001, 1681–1687; Vicente, M. G. H. et al., *Chem. Commun.* 1998, 2355–2356), (5) chlorin-chlorin dimers (Arnold, D. P. et al., *Tetrahedron* 2001, 57, 1335–1345; Zheng, G. et al., *J. Org. Chem.* 2000, 65, 543–557; Osuka, A. et al., *Heterocycles* 1997, 44, 165–168; Jaquinod, L. et al., *Angew. Chem. Int. Ed. Engl.* 1996, 35, 1013–1016), (6) oxochlorin-containing dyads (Kessel, D. et al., *Photochem. Photobiol.* 1991, 53, 475–479; Osuka, A. et al., *Bull. Chem. Soc. Jpn.* 1995, 68, 262–276; Osuka, A. et al., *J. Am. Chem. Soc.* 1996, J18, 155–168).

The conversion of chlorins to oxochlorins has little effect on the spectral properties but renders the macrocycle more resistant to oxidation (Chang, C. K. et al., *J. Am. Chem. Soc.* 1986, 108, 1352–1354; Stolzenberg, A. M. et al., *Inorg. Chem.* 1986, 25, 983–991; Zaleski, J. M. et al., *J. Phys. Chem.* 1993, 97, 13206–13215; Osuka, A. et al., *Bull. Chem. Soc. Jpn.* 1993, 66, 3837–3839). The general approach for forming an oxochlorin employs treatment of a β-substituted porphyrin with a suitable oxidizing agent such as hydrogen peroxide followed by acid-catalyzed pinacol rearrangement of the resulting diol (Inhoffen, von H. et al., *Liebigs Ann. Chem.* 1969, 725, 167–176; Bonnet, R. et al., *J. Chem. Soc. (C)* 1969, 564–570; Chang, C. K. *Biochemistry* 1980, 19, 1971–1976; Chang, C. K. et al., *J. Org. Chem.* 1986, 51, 2134–2137) or $OsO_4$ (Chang, C. K. et al., *J. Org Chem.* 1985, 50, 4989–4991; Chang, C. K. et al., *Heterocyclic Chem.* 1985, 22, 1739–1741; Chang, C. K. et al., *J. Biol. Chem.* 1986, 261, 8593–8596; Bruickner, C. et al., *Tetrahedron Lett.* 1995, 36, 3295–3298; Bruickner, C. et al., *Tetrahedron Lett.* 1995, 36, 9425–9428; Pandey, R. K. et al., *J. Org. Chem.* 1997, 62, 1463–1472). This procedure works well with those porphyrins that give rise to only one oxochlorin isomer. Although this method takes advantage of porphyrins as readily available starting materials, multiple oxochlorin isomers are obtained from porphyrins that possess any of the following structural features: (1) at least one of the four pyrrole rings bears substituents that are different from the others, in which case multiple products are formed due to the reaction of $OSO_4$ at different sites; (2) different substituents (e.g., methyl/ethyl) are present at the two β-positions of the pyrrole ring that is attacked by $O_sO_4$, in which case pinacol rearrangement gives multiple products; and (3) the presence of meso-substituents that cause the symmetry of the porphyrin to be less than four-fold, in which case pinacol rearrangement of the diol gives multiple products. Oxochlorins of the latter type have been incorporated in a few multi-pigment arrays for studies of energy and electron transfer (Osuka, A. et al., *Bull. Chem. Soc. Jpn.* 1995, 68, 262–276; Osuka, A. et al., *J. Am. Chem. Soc.* 1996, 118, 155–168).

SUMMARY OF THE INVENTION

A method of making an oxochlorin comprises the steps of oxidizing a chlorin to produce a mixture of hydroxychlorin and oxochlorin, and then oxidizing the hydroxychlorin in said mixture, preferably with DDQ, to produce a mixture consisting essentially of oxochlorin. The step of oxidizing a chlorin is carried out by exposing the chlorin to alumina, typically in the presence of an oxidizing agent such as air or alumina. The oxidizing steps may be carried out in an organic solvent such as toluene. The chlorin is preferably a C-methylated chlorin, and is preferably metalated.

Also disclosed herein are novel oxochlorin compounds, wherein the oxochlorin compounds are 5,15 trans-substituted or 10,20 trans-substituted with linking groups.

The foregoing and other objects and aspects of the present invention are explained in detail in the specification set forth below.

DETAILED DESCRIPTION OF PREFERRED EMBODIMENTS

Figure 1:
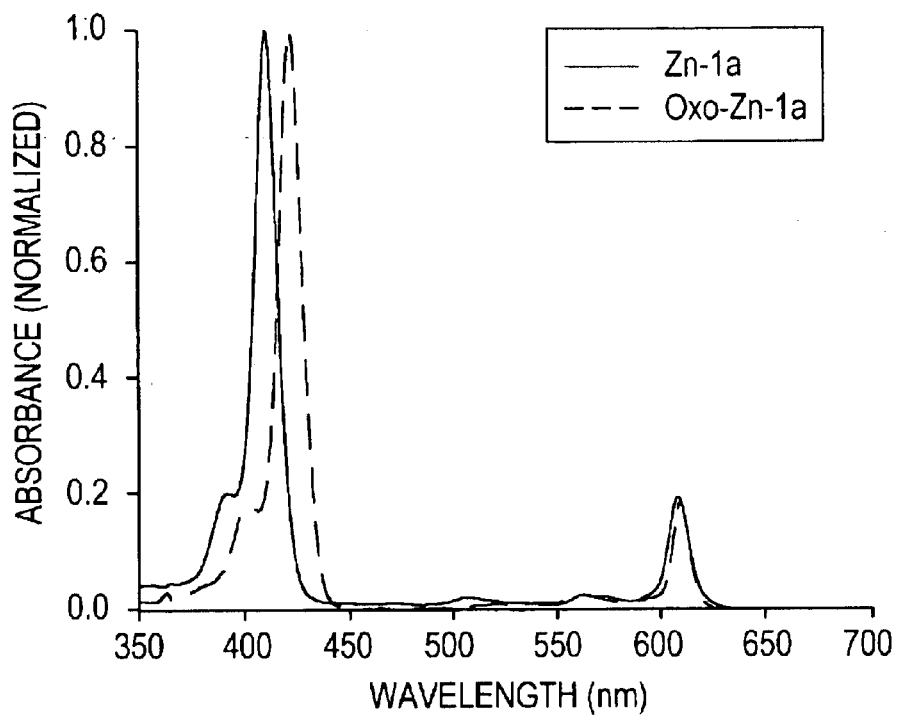
FIG. 1 illustrates the absorption spectra of chlorin Zn-1$a$ and oxochlorin Oxo-Zn-1$a$ in toluene at room temperature.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

"DDQ" as used herein refers to 2,3-dichloro-5,6-dicyano-1,4-benzoquinone.

The term "substituent" as used in the formulas herein, particularly designated by S or S$^n$ where n is an integer, in a preferred embodiment refer to electron-rich or electron-deficient groups (subunits) that can be used to adjust the redox potential(s) of the subject compound. Preferred substituents include, but are not limited to, H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In certain embodiments, a substituted aryl group is attached to a porphyrin or a porphyrinic macrocycle, and the substituents on the aryl group are selected from the group consisting of aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. Additional substituents include, but are not limited to, 4-chlorophenyl, 4-trifluoromethylphenyl, and 4-methoxyphenyl. Preferred substituents provide a redox potential range of less than about 5 volts, preferably less than about 2 volts, more preferably less than about 1 volt.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl group, while acting as substituent can itself have additional substituents (e.g the substituents provided for s$^n$ in the various formulas herein).

The term "alkyl" refers to a paraffinic hydrocarbon group, typically C1 to C4, which may be derived from an alkane by dropping one hydrogen from the formula. Examples are methyl ($CH_3$—), ethyl ($C_2H_5$—), propyl ($CH_3CH_2CH_2$—), isopropyl (($CH_3)_2CH$—).

The term "alkenyl" refers to a hydrocarbon group, typically C2 to C4, derived from the corresponding alkyl and which contains at least one double bond (e.g., butadienyl).

The term "alkynyl" refers to a hydrocarbon group, typically C2 to C4, derived from the corresponding alkyl and which contains at least one triple bond (e.g., butadiynyl).

The term "halogen" refers to one of the electronegative elements of group VIIA of the periodic table (fluorine, chlorine, bromine, iodine, astatine).

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CR unit is replaced with a nitrogen atom.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the —OH of the carboxyl group is replaced by some other substituent (RCO—). Examples include, but are not limited to acetyl, benzoyl, etc.

In preferred embodiments, when a metal is designated by "M" or "M$^n$", where n is an integer, it is recognized that the metal may be associated with a counterion.

A linker is a molecule used to couple two different molecules, two subunits of a molecule, or a molecule to a substrate. When all are covalently linked, they form units of a single molecule.

A "chlorin" is essentially the same as a porphyrin, but differs from a porphyrin in having one partially saturated pyrrole ring. The term porphyrin refers to a cyclic structure typically composed of four pyrrole rings together with four nitrogen atoms and two replaceable hydrogens for which various metal atoms can readily be substituted. A typical porphyrin is hemin. Examples of chlorins that may be used to carry out the present invention include but are not limited to those of Formula X:

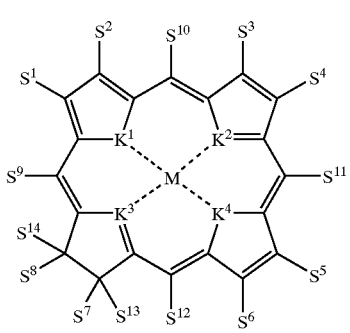

(X)

wherein:
M is a metal selected from the group consisting of Zn, Mg, Pt, Pd, Sn and Al, or M is absent;
$K^1$, $K^2$, $K^3$, and $K^4$ are hetero atoms independently selected from the group consisting of N, O, S, Se, Te, and CH;
$S^1, S^2, S^3, S^4, S^5, S^6, S^7, S^8, S^9, S^{10}, S^{11}, S^{12}, S^{13}$, and $S^{14}$ are independently selected from the group consisting of H, aryl, phenyl, alkyl, cycloalkyl, spiroalkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and optionally either $S^1$ and $S^5$ are trans-substituted linking groups $Q^1$ and $Q^2$, $S^2$ and $S^6$ are trans-substituted linking groups $Q^1$ and $Q^2$, $S^{10}$ and $S^{12}$ are trans-substituted linking groups $Q^1$ and $Q^2$, or $S^9$ and $S^{11}$ are trans-substituted linking groups $Q^1$ and $Q^2$; and $Q^1$ and $Q^2$ are independently selected linking groups of the formula:

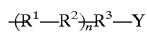

wherein:
n is from 0 or 1 to 5 or 10;
$R^3$ may be present or absent;
$R^1$, $R^2$, and $R^3$ are each independently selected from the group consisting of ethene, ethyne, aryl, and heteroaryl groups, which aryl and heteroaryl groups may be unsubstituted or substituted one or more times with H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl; and Y is a protected or unprotected reactive substituent selected from the group consisting of hydroxy, thio, seleno, telluro, ester, carboxylic acid, boronic acid, phenol, silane, sulfonic acid, phosphonic acid, alkylthiol, formyl, halo, alkenyl, alkynyl, haloalkyl, dialkyl phosphonate, alkyl sulfonate, alkyl carboxylate, acetylacetone ("acac") and dialkyl boronate groups.

In a preferred embodiment neither $S^8$ nor $S^{14}$ in Formula X above is H.

In particular embodiments, $S^1$ and $S^5$ are trans-substituted linking groups $Q^1$ and $Q^2$, or $S^2$ and $S^6$ are trans-substituted linking groups $Q^1$ and $Q^2$.

In other particular embodiments, $S^{10}$ and $S^{12}$ are trans-substituted linking groups $Q^1$ and $Q^2$, or $S^9$ and $S^{11}$ are trans-substituted linking groups $Q^1$ and $Q^2$. When present on oxochlorins, such trans substituted chlorins are novel compounds and are a further aspect of the present invention.

In preferred embodiments of the foregoing, M is present. When present, M is preferably Zn or Mg.

In certain embodiments, $K^1$, $K^2$, $K^3$, and $K^4$ are independently selected from the group consisting of N, O, S, and CH. In particular embodiments, $K^1$, $K^2$, $K^3$, and $K^4$ are all N.

In certain embodiments of the invention, $S^4$, $S^7$, $S^8$, $S^9$, $S^{10}$, $S^{11}$, $S^{12}$, $S^{13}$, and $S^{14}$ in the chlorin of Formula X are all alkyl.

Conversion of the chlorin to the hydroxychlorin may be carried out in any suitable organic solvent, preferably an aromatic solvent, including but not limited to toluene, benzene, chlorobenzene, xylene, mesitylene, etc. Toluene is currently preferred. In particular reactions attempted $CH_2Cl_2$ did not work, but more polar chlorins may require a more polar solvent. Potentially, without wishing to be bound to any particular theory for the invention, the solvent should dissolve the chlorin but not be such a strong solvent as to interfere with binding of the chlorin to the alumina. Accordingly, for polar chlorins, solvents such as $CH_2Cl_2$, acetonitrile, etc. may be satisfactory. The chlorin may be included in any suitable amount, such as 1 mM to 100 mM or more. 20 mM is currently preferred. The reaction may be carried out at any suitable temperature, such as (for example) 0 to 100° C. A temperature of 60° C. is currently preferred.

Conversion of the hydroxychlorin to the oxochlorin may be carried out in DDQ as noted above. The DDQ may be included in any suitable concentration, such as 0.1 or 0.3 mM to 1 M or more. The hydroxychlorin may be included in any suitable amount, such as 0.1 mM to 0.4 M or more. The reaction may be carried out at any suitable temperature, such as from 0 to 100° C. Room temperature is currently preferred.

Solvents may be as above, with toluene currently preferred, and with more polar solvents potentially being more desirable for more polar chlorins.

Oxochlorins of the present invention may be used as building blocks for the production of polymers thereof, with other chlorins, oxochlorins, porphyrinic macrocycles or the like, in accordance with a variety of techniques, including but not limited to:

Glaser (or Eglinton) coupling of a monomeric pigment building blocks (generating a butadiyne linker)

Cadiot-Chodkiewicz coupling of two different pigment building blocks (generating a butadiyne linker joining a block copolymer)

Sonogashira coupling of two different pigment building blocks (generating an ethyne linker joining a block copolymer)

Heck or Wittig reactions of two different pigment building blocks (generating an alkene linker joining a block copolymer)

Suzuki coupling of two different pigment building blocks (generating a phenylene or biphenyl linker joining a block copolymer)

Polymerization of pigment building blocks bearing substituents such as two or more thiophene groups (generating an oligothiophene linker) or two or more pyrrole groups (generating a polypyrrole linker).

Oxochlorin monomers and oxochlorin-containing polymers of the present invention are useful for the production of light harvesting arrays and solar cells when immobilized on electrodes, and as active agents for photodynamic therapy. Solar cells of the present invention can be used in a variety of different electrical devices. Such devices typically comprise a solar cell as described above, and a circuit (e.g., a resistive load) electrically coupled to said solar cell (e.g., by providing a first electrical coupling of the circuit to one electrode of the solar cell, and a second electrical coupling of the circuit to the other electrode of the solar cell).

The examples, which follow, are set forth to illustrate the present invention, and are not to be construed as limiting thereof.

EXAMPLE 1

Experimental Methods

Introduction. A rational synthesis of C-methylated chlorin building blocks (Strachan, J.-P. et al., *J. Org. Chem.* 2000, 65, 3160–3172; Balasubramanian, T. et al., *J. Org. Chem.* 2000, 65, 7919–7929; Taniguchi, M. et al., *J. Org. Chem.* 2001, 66, 7342–7354) has recently been developed. Each chlorin bears one geminal dimethyl group and one methylene group at the β-positions in the reduced ring. For building block applications, we have previously succeeded in introducing synthetic handles at several β-positions (2, 8, 12) and two meso positions (5, 10). One objective is to incorporate chlorins into soluble linear arrays composed of a large number of chlorins. To reach this objective requires access to chlorins with synthetic handles in a trans architecture and solubilizing groups at one or more of the non-linking positions. The 2,12-positions afford a linear architecture but the synthesis of these chlorin building blocks is lengthy, requiring synthesis of β-substituted pyrroles. Substitution at 5,15-positions or 10,20 positions also affords linear arrays and takes advantage of the more expedient synthesis of meso-substituted dipyrromethanes. With use of the 2,12- or 5,15-positions for synthetic handles, the 10-position has heretofore been employed for incorporating solubilizing groups. It was reasoned that incorporation of substituents at the reduced ring could be used to increase the solubility of chlorins and/or achieve further sites for functionalization. To render the chlorins more resistant to oxidation, we sought to convert the methylene unit of the reduced ring to a keto functionality. In this manner, oxidation occurs at a known site and only one isomer is formed regardless of the substitution pattern at the perimeter of the macrocycle.

Herein is described a new method for converting C-alkylated chlorins to the corresponding oxochlorins. The method has been applied to chlorins bearing a variety of substituents. Several new chlorins and the corresponding oxochlorins have been prepared with novel substituents, including a spiroalkyl unit in place of the geminal dimethyl unit in the reduced ring, a phenyl substituent at the 15-position (adjacent to the oxo moiety in the reduced ring) or at the 20-position (adjacent to the geminal dimethyl unit), and the oxochlorins have been converted to various metalation states (zinc, magnesium, copper, free base). The free base and metallo oxochlorins have been characterized by electrochemistry and static fluorescence spectroscopy. This work provides the foundation for developing oxochlorin building blocks for use in various molecular devices. Furthermore, we describe the synthesis of chlorin-chlorin and oxochlorin-oxochlorin dyads with components in different metalation states. The photophysical and electrochemical characterization of the dyads will furnish fundamental data for consideration of the use of related constructs in larger light-harvesting arrays.

General. All $^1$H NMR spectra (300 or 400 MHz) were obtained in CDCl$_3$ unless noted otherwise. Basic alumina (60–325 mesh, activity grade I) and neutral alumina (80–200 mesh) were obtained from Fisher Scientific. Activity grade V alumina was prepared from grade I alumina (Li, F. et al., *J. Mater. Chem.* 1997, 7, 1245–1262).

Non-commercial compounds. The compounds Zn-1a-e were prepared as described in the literature (Taniguchi, M. et al., *J. Org. Chem.* 2001, 66, 7342–7354).

Spectroscopy. All absorption spectra were recorded in toluene at room temperature on a HP-8453 spectrometer. All emission spectra were recorded in toluene at room temperature on a SPEX FluoroMax spectrometer. Fluorescence quantum yields were determined by ratioing to suitable standards such as Zn-1a ($\Phi_f$=0.065) or Fb-1a ($\Phi_f$=0.29) which in turn related to ZnTPP and Fb-TPP (Strachan, J.-P. et al., *J. Org. Chem.* 2000, 65, 3160–3172). Excitation was performed at 570 nm, 590 nm, or in the Soret region.

Zn(II)-17,18-Dihydro-18,18-dimethyl-5-(4-methylphenyl)-10-mesityl-17-oxoporphyrin (Oxo-Zn-1a). A mixture of Zn-1a (25.0 mg, 41 μmol) and basic alumina (grade I, 1.75 g) in toluene (2 mL) in an amber vial (loosely plugged with cotton) was stirred at room temperature for 36 h. Analysis by TLC (silica, 1:19 mixture of ethyl acetate and CH$_2$Cl$_2$) showed three components: a fast moving blue component (R$_f$=0.82; Zn-1a), a medium-fast moving green component (R$_f$=0.38; Oxo-Zn-1a), and a slow moving blue component (R$_f$=0.15; HO-Zn-1a). Solvent was removed under reduced pressure and the alumina was washed (CH$_2$Cl$_2$/CH$_3$OH, 19:1) until the washings were colorless. The green solution was concentrated and the residue was chromatographed (silica, CH$_2$Cl$_2$), affording Zn-1a (6.0 mg, 24%) as the first fraction and Oxo-Zn-1a (4.0 mg, 16%) as the second fraction. Further elution (CH$_2$Cl$_2$/ethyl acetate, 49:1) gave hydroxychlorin HO-Zn-1a (13.0 mg, 52%). A small fraction containing a mixture of HO-Zn-1*a* and Oxo-Zn-1a was discarded. Similar results were obtained when the reaction was carried out on a 0.2-mmol scale [122 mg of Zn-1a and 8.5 g of basic alumina in 4 mL of toluene gave unchanged Zn-1a (15 mg, 12%), Oxo-Zn-1a (14 mg, 11%) and HO-Zn-1a (73 mg, 58%) after 60 h]. LD-MS for HO-Zn-1a: obsd 625.01, calcd 626.01 (C$_{38}$H$_{34}$N$_4$OZn). Solid DDQ (10.0 mg, 44 μmol) was added to a solution of HO-Zn-1a (10.0 mg, 16 μmol) in toluene (400 μL) in an amber vial. The mixture was stirred for 2 h. Triethylamine (100 μL) was added and the solvent was removed under reduced pressure. The residue was immediately chromatographed (silica, CH$_2$Cl$_2$), affording a green solid (9.0 mg, 90%): IR (CH$_2$Cl$_2$) 1717 cm$^{-1}$; $^1$H NMR δ 1.82 (s, 6H), 2.03 (s, 6H), 2.59 (s, 3H), 2.67 (s, 3H), 7.22 (s, 2H), 7.50 (d, J=8.1 Hz, 2H), 7.98 (d, J=8.1 Hz, 2H) 8.46 (d, J=5.1 Hz, 1H), 8.54 (d, J=4.2 Hz, 1H) 8.64 (d, J=4.2 Hz, 1H), 8.83 (d, J=4.5 Hz, 1H), 8.89 (m, 3H), 9.55 (s, 1H); LD-MS obsd 622.16, calcd 624.1868 (C$_{38}$H$_{32}$N$_4$OZn); λ$_{abs}$ 423 (log ε=5.32), 563 (3.82), 609 (4.60) nm; λ$_{em}$ 609, 650, 669 nm (Φ$_f$=0.028).

In a repeat run, a mixture of Zn-1a (5.0 mg, 8 μmol) and basic alumina (350 mg) in toluene (0.5 mL) was heated at 50° C. for 15 h. The alumina was removed by filtration and the filtrate was concentrated to dryness. The residue was dissolved in toluene (0.3 mL). DDQ (4.0 mg, 18 μmol) was added and the mixture was stirred for 45 min. Work-up of the reaction mixture as in the previous case yielded Oxo-Zn-1a (2.7 mg, 54%) as the only isolable product.

Zn(II)-17,18-Dihydro-18,18-dimethyl-17-oxo-5,10-bis (pentafluorophenyl)porphyrin (Oxo-Zn-1b). A mixture of chlorin Zn-1b (21.0 mg, 28.5 μmol) and basic alumina (activity I, 1.40 g) in toluene (0.75 mL) in an amber vial (loosely plugged with cotton) was stirred for 120 h. Solvent was removed under reduced pressure and the residue was washed (CH$_2$Cl$_2$/CH$_3$OH, 19:1) until the washings were colorless. Solvent was removed and the residue was chromatographed (silica). Elution with hexanes/CH$_2$Cl$_2$ (1:4) gave Zn-1b (8.0 mg, 38%); elution with CH$_2$Cl$_2$ gave Oxo-Zn-1b (3.0 mg, 14%); elution with CH$_2$Cl$_2$/ethyl acetate (49:1) gave hydroxychlorin HO-Zn-1b (7.0 mg, 33%). LD-MS data for HO-Zn-1b: obsd 752.72 calcd 750.05 (C$_{34}$H$_{16}$F$_{10}$N$_4$OZn). Solid DDQ (4.2 mg, 18 μmol) was added to a solution of HO-Zn-1b (7.0 mg, 9 μmol) in toluene (200 μL) in an amber vial. The mixture was stirred for 45 min. Triethylamine (100 μL) was added and the solvent was removed under reduced pressure. The residue was immediately chromatographed (silica, CH$_2$Cl$_2$) affording a green solid (5.2 mg, 74%): IR (CH$_2$Cl$_2$) 1719 cm$^{-1}$; $^1$H NMR δ 1.94 (s, 6H), 8.56 (d, J=4.8 Hz, 1H), 8.61 (d, J=4.8 Hz, 1H), 8.74 (m, 2H) 9.03 (d, J=4.8 Hz, 1H), 9.07 (d, J=4.8 Hz, 1H), 9.08 (s, 1H), 9.60 (s, 1H); LD-MS obsd 746.43, calcd 748.0299 (C$_{34}$H$_{14}$F$_{10}$N$_4$OZn); λ$_{abs}$ 423 (log ε=5.23), 567 (3.80), 613 (4.54) nm; λ$_{em}$ 614, 653, 671 nm (Φ$_f$=0.024).

In a repeat run, a mixture of Zn-1b (15.0 mg, 20 μmol) and DDQ (28.0 mg, 120 μmol) in toluene (2 mL) was stirred at room temperature for 4 h. Triethylamine (200 μL) was added and stirring was continued for 30 min. The mixture was filtered, solvent was removed under reduced pressure and the residue was worked up in the usual manner to yield 5.0 mg (33%) of Oxo-Zn-1b and 1.0 mg (7%) of HO-Zn-1b.

Zn(II)-17,18-Dihydro-18,18-dimethyl-5-(4-methylphenyl)-10-{4-[2-(trimethylsilyl)ethoxycarbonyl] phenyl}-17-oxoporphyrin (Oxo-Zn-1c). A mixture of Zn-1c (25.0 mg, 35.0 μmol) and basic alumina activity 1 (1.5 g) in 2 mL toluene was stirred for 4 h at 50° C. After standard workup, the residue was dissolved in 1.5 mL of toluene and 2.5 equiv of DDQ (19.9 mg, 87.5 μmol) was added. Standard workup and chromatography [silica, ethyl acetate/CH$_2$Cl$_2$ (1:5)] gave a bluish-purple solid (8.2 mg, 31%): $^1$H NMR δ 0.17 (s, 9H), 1.22–1.27 (m, 2H), 2.04 (s, 6H), 2.68 (s, 3H), 4.47–4.54 (m, 2H), 7.52 (d, J=8.0 Hz, 2H), 7.97 (d, J=8.0 Hz, 2H), 8.15 (d, J=8.0 Hz, 2H), 8.30 (d, J=8.0 Hz, 2H), 8.54 (d, J=4.4 Hz, 1H), 8.61 (d, J=4.4 Hz, 1H), 8.72 (d, J=4.4 Hz, 1H), 8.86 (d, J=4.4 Hz, 1H), 8.93 (d, J=4.4 Hz, 1H), 8.97 (d, J=4.4 Hz, 1H), 8.98 (s, 1H), 9.56 (s, 1H); LD-MS obsd 727.45; FAB-MS obsd 726.2020, calcd 726.2005 (C$_{41}$H$_{38}$N$_4$O$_3$SiZn); λ$_{abs}$ 425 (log ε=5.39), 564 (3.96), 610 (4.62) nm; λ$_{em}$ 610, 651, 669 nm (Φ$_f$=0.030).

17,18-Dihydro-18,18-dimethyl-5-(4-methylphenyl)-10-mesityl-17-oxoporphyrin (Oxo-Fb-1a). TFA (40 μL) was added to a solution of Oxo-Zn-1a (6.2 mg, 9.6 μmol) in CH$_2$Cl$_2$ (400 μL) and the mixture was stirred for 30 min. The reaction was monitored by absorption spectroscopy. The reaction mixture was diluted with ethyl acetate and washed with saturated aqueous NaHCO$_3$. The organic layer was separated, dried (MgSO$_4$), concentrated, and chromatographed over silica affording a green solid (5.2 mg, 93%): IR (CH$_2$Cl$_2$) 3344 and 1720 cm$^{-1}$; $^1$H NMR δ −2.18 (s, 1H), −2.27 (s, 1H), 1.85 (s, 6H), 2.11 (s, 6H), 2.63 (s, 3H), 2.70 (s, 3H), 7.55 (d, J=7.2 Hz, 2H), 8.04 (d, J=7.2 Hz, 2H), 8.50 (d, J=4.5 Hz, 2H), 8.58 (d, J=4.5 Hz, 2H), 8.74 (d, J=4.5 Hz, 1H), 8.94 (d, J=4.5 Hz, 1H) 9.08 (d, J=4.5 Hz, 1H), 9.11 (d, J=4.5 Hz, 1H) 9.21 (s, 1H), 9.82 (s, 1H); LD-MS obsd 560.08, calcd 562.2733 (C$_{38}$H$_{34}$N$_4$O); λ$_{abs}$ 414 (log ε=5.24), 512 (4.10), 545 (3.86), 586 (3.74), 643 (4.31) nm; λ$_{em}$ 643, 685, 713 nm (Φ$_f$=0.064).

17,18-Dihydro-18,18-dimethyl-17-oxo-5,10-bis (pentafluorophenyl)porphyrin (Oxo-Fb-1b). TFA (40 μL) was added to a solution of Oxo-Zn-1b (7.5 mg) in CH$_2$Cl$_2$ (400 μL) and the mixture was stirred for 2 h. Standard workup and chromatography (silica) gave a green solid: IR (CH$_2$Cl$_2$) 3345 and 1725 cm$^{-1}$; $^1$H NMR δ −2.75 (s, 1H), −2.63 (s, 1H), 2.11 (s, 6H), 8.66 (d, J=4.8 Hz, 1H), 8.74 (d, J=4.5 Hz, 1H), 8.89 (t, 2H), 9.27 (dd, 1H), 9.31 (dd, 1H), 9.43 (s, 1H), 10.01 (s, 1H); LD-MS obsd 686.26, calcd 686.1164 (C$_{34}$H$_{16}$F$_{10}$N$_4$O); λ$_{abs}$ 413 (log ε=5.08), 508 (3.99), 541 (3.71), 592 (3.60), 645 (4.30) nm; λ$_{em}$ 645, 686, 715 nm (Φ$_f$=0.067).

17,18-Dihydro-18,18-dimethyl-5-(4-methylphenyl)-10-{4-[2-(trimethylsilyl)ethoxycarbonyl]phenyl}-17-oxoporphyrin (Oxo-Fb-1c). To a solution of Oxo-Zn-1c (6.5 mg, 8.9 μmol) in CH$_2$Cl$_2$ (5 mL) was added a 50-fold excess of TFA. Standard workup and chromatography [silica, hexanes/CH$_2$Cl$_2$ (2:1)] gave a purple solid (5.4 mg, 91%): $^1$H NMR δ −2.46—−2.42 (br, 1H), −2.31—−2.27 (br, 1H), 0.17 (s, 9H), 1.26–1.32 (m, 2H), 2.11 (s, 6H), 2.70 (s, 3H), 4.59–4.63 (m, 2H), 7.55 (d, J=8.0 Hz, 2H), 8.02 (d, J=8.0 Hz, 2H), 8.23 (d, J=8.0 Hz, 2H), 8.44 (d, J=8.0 Hz, 2H), 8.56 (d, J=4.8 Hz, 1H), 8.62 (d, J=4.8 Hz, 1H), 8.84 (d, J=4.8 Hz, 1H), 8.96 (d, J=4.8 Hz, 1H), 9.10 (d, J=4.8 Hz, 1H), 9.17 (d, J=4.8 Hz, 1H), 9.25 (s, 1H), 9.86 (s, 1H); LD-MS obsd 663.06; FAB-MS obsd 665.2961, calcd 665.2948 (C$_{41}$H$_{40}$N$_4$O$_3$Si) [M+H]$^+$; λ$_{abs}$ 416 (log ε=5.28), 513 (4.10), 547 (3.92), 593 (3.79), 643 (4.25) nm; λ$_{em}$ 643, 686, 713 nm (Φ$_f$=0.14).

Mg(II)-17,18-Dihydro-10-mesityl-18,18-dimethyl-5-(4-methylphenyl)porphyrin (Mg-1a). Following a standard procedure, a mixture of Fb-1a (5.0 mg, 9.1 μmol), MgI$_2$ (25 mg, 89 μmol), and N,N-diisopropylethylamine (31 μl, 178 μmol) in CH$_2$Cl$_2$ (500 μL) was stirred for 3 h. The fluorescence excitation spectrum of an aliquot taken at this stage indicated total consumption of Fb-1a. The mixture was treated with 10% aqueous NaHCO$_3$. The organic layer was separated, dried (Na$_2$SO$_4$), and concentrated. The title compound underwent demetalation during work up. A peak corresponding to M$^+$ was not visible in the LD-MS spectrum of this sample.

Mg(II)-17,18-Dihydro-10-mesityl-18,18-dimethyl-5-(methylphenyl)-17-oxoporphyrin (Oxo-Mg-1a). A mixture of Oxo-Fb-1a (5.0 mg, 8.9 μmol), MgI$_2$ (25 mg, 89 μmol), and N,N-diisopropylethylamine (31 μL, 178 μmol) in CH$_2$Cl$_2$ (500 μL) was stirred for 3 h. Standard workup and chromatography [basic alumina, grade V, CH$_2$Cl$_2$/methanol (199:1)] gave a green solid (2.0 mg, 38%): LD-MS obsd 583.67, calcd 584.2427 (C$_{38}$H$_{32}$N$_4$OMg); λ$_{abs}$ 425 (log ε=5.28), 568 (3.92), 617 (4.54) nm; λ$_{em}$ 617, 659, 672 nm (Φ$_f$=0.056).

Cu(II)-17,18-Dihydro-10-mesityl-18,18-dimethyl-5-(4-methylphenyl)porphyrin (Cu-1a). To a solution of Fb-1a (20 mg, 36 μmol) in CH$_2$Cl$_2$ (18 mL) was added a solution of Cu(OAc)$_2$·H$_2$O in methanol (160 mg, 800 μmol in 2 mL). The mixture was stirred overnight. Solvent was removed and the residue was suspended in a mixture (1:1) of hexanes and CH$_2$Cl$_2$. After sonication, the mixture was filtered. The filtrate was concentrated and chromatographed [silica, CH$_2$Cl$_2$/hexanes (2:3)] affording a blue solid (19 mg, 85%): LD-MS obsd 611.82, calcd 609.2176 (C$_{38}$H$_{34}$CuN$_4$); λ$_{abs}$ 408 (log ε=5.21), 501 (3.70), 569 (3.81), 605 (4.43) mm.

Cu(II)-17,18-Dihydro-18,18-dimethyl-5,10-bis(pentafluorophenyl)porphyrin (Cu-1b). To a solution of Fb-1b (4.1 mg, 6.1 μmol) in CH$_2$Cl$_2$ (2 mL) was added a solution of Cu(OAc)$_2$·H$_2$O in methanol (100 mg, 500 μmol in 0.5 mL). The mixture was stirred for 36 h. Standard workup and chromatography [silica, CH$_2$Cl$_2$/hexanes (2:3)] gave a blue solid (3.8 mg, 87%): LD-MS obsd 733.07, calcd 733.061 1(C$_{34}$H$_{16}$CuF$_{10}$N$_4$); λ$_{abs}$ 410 (log ε=5.23), 505 (3.60), 568 (3.78), 611 (4.54) nm.

Cu(II)-17,18-Dihydro-10-mesityl-18,18-dimethyl-5-(4-methylphenyl)-17-oxoporphyrin (Oxo-Cu-1a). To a solution of Oxo-Fb-1a (3.4 mg, 6.1 μmol) in CH$_2$Cl$_2$ (2.5 mL) was added a solution of Cu(OAc)$_2$·H$_2$O in methanol (120 mg, 600 μmol in 0.5 mL). The mixture was stirred at room temperature for 36 h followed by warming at 35° C. for 6 h. Standard workup and chromatography (silica, CH$_2$Cl$_2$) gave a blue solid (3.1 mg, 82%): LD-MS obsd 623.00, calcd 623.1972 (C$_{38}$H$_{32}$CuN$_4$O); λ$_{abs}$ 419 (log ε=5.24), 605 (4.43) nm.

Cu (II)-17,18-Dihydro-18,18-dimethyl-17-oxo-5,10-bis(pentafluorophenyl)porphyrin (Oxo-Cu-1b). To a solution of Oxo-Fb-1b (2.9 mg, 4.2 μmol) in CH$_2$Cl$_2$ (2.5 mL) was added a solution of Cu(OAc)$_2$·H$_2$O in methanol (100 mg, 500 μmol in 0.5 mL). The mixture was stirred at room temperature for 48 h followed by warming at 35° C. for 6 h. Standard workup and chromatography (silica, CH$_2$Cl$_2$) gave a blue solid (2.3 mg, 73%): LD-MS obsd 745.66, calcd 747.0404 (C$_{34}$H$_{14}$CuN$_4$O); λ$_{abs}$ 418 (log ε=5.27), 610 (4.51) nm.

17,18-Dihydro-18,18-dimethyl-5-(4-methylphenyl)-10-{4-[2-(trimethylsilyl)ethoxycarbonyl]phenyl}porphyrin (Fb-1c). A solution of Zn-1c (16.0 mg, 22.4 μmol) in 5 mL of CH$_2$Cl$_2$ was added a 50-fold excess of TFA. The demetalation was complete in 1 h as confirmed by UV-Vis and TLC analyses. Standard workup and chromatography [silica, hexanes/CH$_2$Cl$_2$ (1:1)] gave a reddish purple solid (10.8 mg, 74%): $^1$H δ −1.94−−1.87 (br, 2H), 0.17 (s, 9H), 1.25−1.32 (m, 2H), 2.06 (s, 6H), 2.67 (s, 3H), 4.53−4.64 (m, 2H), 4.62 (s, 2H), 7.51 (d, J=7.6 Hz, 2H), 8.00 (d, J=7.6 Hz, 2H), 8.20 (d, J=8.0 Hz, 2H), 8.38 (d, J=8.0 Hz, 2H), 8.40 (d, J=4.4 Hz, 1H), 8.51 (d, J=4.4 Hz, 1H), 8.70 (d, J=4.8 Hz, 1H), 8.78−8.82 (m, 2H), 8.84 (d, J=4.8 Hz, 1H), 8.88 (s, 1H), 8.97 (s, 1H); LD-MS obsd 649.96; FAB-MS obsd 651.3171, calcd 651.3155 (C$_{41}$H$_{42}$N$_4$O$_2$Si) [M+H]$^+$; λ$_{abs}$ 415 (log ε=5.58), 509 (4.54), 589 (3.09), 640 (4.97) nmn; λ$_{em}$ 641, 683, 707 nm (Φ$_f$=0.28).

5-(3,5-Di-tert-butylphenyl)-10-[4-[2-ethynyl]phenyl]-7,18-dihydro-18,18-dimethylporphyrin (Fb-1d). A solution of Zn-1d (22.0 mg, 31.8 μmol) in 10 mL of CH$_2$Cl$_2$ was added a 50-fold excess of TFA. Standard workup and chromatography [silica, hexanes/CH$_2$Cl$_2$ (2:1)] gave a reddish purple solid (12.5 mg, 62%): $^1$H NMR δ −1.88−−1.84 (br, 2H), 1.50 (s, 18H), 2.06 (s, 6H), 3.29 (s, 1H), 4.62 (s, 2H), 7.75 (t, J=1.6 Hz, 1H), 7.84 (d, J=7.6 Hz, 2H), 7.97 (d, J=1.6 Hz, 2H), 8.09 (d, J=7.6 Hz, 2H), 8.44 (d, J=4.4 Hz, 1H), 8.53 (d, J=4.4 Hz, 1H), 8.72 (d, J=4.8 Hz, 1H), 8.80 (d, J=4.8 Hz, 1H), 8.81−8.85 (m, 2H), 8.87 (s, 1H), 8.96 (s, 1H); LD-MS obsd 627.09; FAB-MS obsd 628.3550, calcd 628.3566 (C$_{44}$H$_{44}$N$_4$); λ$_{abs}$ 416 (log ε=5.16), 510 (4.13), 590 (3.67), 641 (4.54) nm; λ$_{em}$ 641, 683, 707 nm (Φ$_f$=0.29).

5-(3,5-Di-tert-butylphenyl)-17,18-dihydro-10-(4-iodophenyl)-18,18-dimethylporphyrin (Fb-1e). A solution of Zn-1e (67.6 mg, 85.1 μmol) in 25 mL of CH$_2$Cl$_2$ was added a 50-fold excess of TFA. Standard workup and chromatography [silica, hexanes/CH$_2$Cl$_2$ (3:1)] gave a reddish purple solid (43.7 mg, 70%): $^1$H NMR δ −1.92−−1.84 (br, 2H), 1.50 (s, 18H), 2.06 (s, 6H), 4.61 (s, 2H), 7.75 (t, J=1.5 Hz, 1H), 7.86 (d, J=8.1 Hz, 2H), 7.97 (d, J=1.5 Hz, 2H), 8.04 (d, J=8.1 Hz, 2H), 8.44 (d, J=4.4 Hz, 1H), 8.53 (d, J=4.4 Hz, 1H), 8.72 (d, J=5.1 Hz, 1H), 8.79 (d, J=5.1 Hz, 1H), 8.80−8.86 (m, 2H), 8.87 (s, 1H), 8.96 (s, 1H); LD-MS obsd 729.33; FAB-MS obsd 730.2539, calcd 730.2532 (C$_{42}$H$_{43}$IN$_4$); λ$_{abs}$ 416 (log ε=5.19), 510 (4.16), 592 (3.71), 641 (4.59) nm; λ$_{em}$ 641, 683, 708 nm (Φ$_f$=0.092).

Zn(II)-5-(3,5-Di-tert-butylphenyl)-10-[4-[2-ethynyl]phenyl]-7,18-dihydro-18,18-dimethyl-17-oxoporphyrin (Oxo-Zn-1d). A mixture of Zn-1d (50.0 mg, 72.2 μmol) and basic alumina activity 1 (3 g) in 4 mL toluene was stirred for 8 h at 50° C. TLC analysis of the reaction mixture showed that all the starting material was consumed. The alumina was removed by filtration and was washed with CH$_2$Cl$_2$/methanol (19/1) until the washings were colorless. The filtrate was concentrated and dissolved in toluene (40 mL), then 2 equiv of DDQ (32.7 mg, 144 μmol) was added. The mixture was stirred for 5 min and then triethylamine (0.1 mL) was added. The solvent was removed under vacuum. Chromatography of the residue (silica, CH$_2$Cl$_2$) afforded a bluish purple solid (30.4 mg, 60%): $^1$H NMR δ 1.51 (s, 18H), 2.01 (s, 6H), 3.30 (s, 1H), 7.77 (t, J=1.6 Hz, 1H), 7.84 (d, J=8.4 Hz, 2H), 7.95 (d, J=1.6 Hz, 2H), 8.07 (d, J=8.4 Hz, 2H), 8.59 (d, J=4.4 Hz, 1H), 8.64 (d, J=4.4 Hz, 1H), 8.76 (d, J=4.4 Hz, 1H), 8.88 (d, J=4.4 Hz, 1H), 8.94 (d, J=4.4 Hz, 1H), 8.97 (s, 1H), 8.98 (d, J=4.4 Hz, 1H), 9.51 (s, 1H); LD-MS obsd 704.88; FAB-MS obsd 704.2507, calcd 704.2494 (C$_{44}$H$_{40}$N$_4$OZn); λ$_{abs}$ 426 (log ε=5.40), 564 (4.01), 610 (473) nm; λ$_{em}$ 610, 650, 668 nm (Φ$_f$=0.030).

Zn(II)-5-(3,5-Di-tert-butylphenyl)-17,18-dihydro-10-(4-iodophenyl)-18,18-dimethyl-17-oxoporphyrin (Oxo-Zn-1e). A mixture of Zn-1e (75.0 mg, 94.4 μmol) and basic alumina activity I (4.5 g) in 6 mL toluene was stirred for 5 h at 50° C. After standard workup, the residue was dissolved in toluene (60 mL) and 2 equiv of DDQ (42.9 mg, 189 μmol) was added. Standard workup and chromatography [silica, hexanes/CH$_2$Cl$_2$ (1:3)] gave a bluish purple solid (49.8 mg, 65%): $^1$H NMR δ 1.51 (s, 18H), 2.06 (s, 6H), 7.77 (t, J=1.6 Hz, 1H), 7.84 (d, J=8.4 Hz, 2H), 7.94 (d, J=1.6 Hz, 2H), 8.05 (d, J=8.4 Hz, 2H), 8.60 (d, J=4.4 Hz, 1H), 8.63 (d, J=4.4 Hz, 1H), 8.78 (d, J=4.4 Hz, 1H), 8.88 (d, J=4.4 Hz, 1H), 8.94 (d, J=4.4 Hz, 1H), 8.98 (s, 1H), 9.00 (d, J=4.4 Hz, 1H), 9.61 (s, 1H); LD-MS obsd 804.57; FAB-MS obsd 806.1472, calcd 806.1460 (C$_{42}$H$_{39}$IN$_4$OZn); λ$_{abs}$ 425 (log ε=5.25), 563 (3.84), 609 (4.49) un; λ$_{em}$ 610, 649, 668 nm (Φ$_f$=0.013).

5-(3,5-Di-tert-butylphenyl)-10-[4-[2-ethynyl]phenyl]-17,18-dihydro-18,18-dimethyl-17-oxoporphyrin (Oxo-Fb-1d). A 50-fold excess of TFA was added to a solution of Oxo-Zn-1d (9.8 mg, 14 μmol) in CH$_2$Cl$_2$ (5 mL). Standard workup and chromatography [silica, hexanes/CH$_2$Cl$_2$ (1:1)] gave a reddish purple solid (7.5 mg, 86%): $^1$H NMR δ −2.40−−2.36 (br, 1H), −2.27−−2.24 (br, 1H), 1.52 (s, 18H), 2.11 (s, 6H), 3.32 (s, 1H), 7.80 (t, J=1.6 Hz, 1H), 7.88 (d, J=8.0 Hz, 2H), 7.99 (d, J=1.6 Hz, 2H), 8.13 (d, J=8.0 Hz, 2H), 8.60 (d, J=4.4 Hz, 1H), 8.63 (d, J=4.4 Hz, 1H), 8.87 (d, J=4.4 Hz, 1H), 8.97 (d, J=4.4 Hz, 1H), 9.10 (d, J=4.4 Hz, 1H), 9.17 (d, J=4.4 Hz, 1H), 9.23 (s, 1H), 9.85 (s, 1H); LD-MS obsd 641.80; FAB-MS obsd 643.3448, calcd 643.3437 ($C_{44}H_{42}N_4O$) [M+H]$^+$; $\lambda_{abs}$ 417 (log $\epsilon$=5.30), 514 (4.10), 550 (3.92), 593 (3.77), 643 (4.25) nm; $\lambda_{em}$ 643, 686, 713 nm ($\Phi_f$=0.14).

5-(3,5-Di-tert-butylphenyl)-17,18-dihydro-10-(4-iodophenyl)-18,18-dimethyl-17-oxoporphyrin (Oxo-Fb-1e). A 50-fold excess of TFA was added to a solution of Oxo-Zn-1e (10.2 mg, 12.6 μmol) in $CH_2Cl_2$ (5 mL). Standard workup and chromatography [silica, hexanes/$CH_2Cl_2$ (2:1)] gave a reddish purple solid (8.4 mg, 90%): $^1$H NMR δ −2.42—−2.38 (br, 1H), −2.29—−2.25 (br, 1H), 1.52 (s, 18H), 2.10 (s, 6H), 7.80 (s, 1H), 7.90 (d, J=7.6 Hz, 2H), 7.99 (s, 2H), 8.09 (d, J=7.6 Hz, 2H), 8.60 (d, J=4.4 Hz, 1H), 8.63 (d, J=4.4 Hz, 1H), 8.87 (d, J=4.4 Hz, 1H), 8.97 (d, J=4.4 Hz, 1H), 9.10 (d, J=4.4 Hz, 1H), 9.17 (d, J=4.4 Hz, 1H), 9.24 (s, 1H), 9.85 (s, 1H); LD-MS obsd 742.81; FAB-MS obsd 745.2429, calcd 745.2403 ($C_{42}H_{41}IN_4O$) [M+H]$^+$; $\lambda_{abs}$ 416 (log $\epsilon$=5.29), 513 (4.11), 547 (3.92), 589 (3.79), 643 (4.26) nm; $\lambda_{em}$ 643, 687, 714 nm ($\Phi_f$=0.049).

Cu(II)-5-(3,5-Di-tert-butylphenyl)-10-[4-[2-ethynyl]phenyl]-17,18-dihydro-18,18-dimethylporphyrin (Cu-1d). A 25-fold excess of Cu(OAc)$_2 \cdot H_2O$ (135 mg, 0.675 mmol) was added to a solution of Fb-1d (17.0 mg, 27.0 μmol) in $CH_2Cl_2$/methanol (4 mL, 1:1). The metalation was complete in 1.5 h as confirmed by UV-Vis and TLC analyses. Standard workup and chromatography [silica, hexanes/$CH_2Cl_2$ (1:1)] gave a blue solid (16.0 mg, 86%): LD-MS obsd 688.68; FAB-MS obsd 689.2736, calcd 689.2705 ($C_{44}H_{42}CuN_4$); $\lambda_{abs}$ (log $\epsilon$=5.31), 500 (3.75), 604 (4.55) nm.

Cu(II)-5-(3,5-Di-tert-butylphenyl)-17,18-dihydro-10-(4-iodophenyl)-18,18-dimethyl-porphyrin (Cu-1e). A 25-fold excess of Cu(OAc)$_2 \cdot H_2O$ (98.8 mg, 0.495 mmol) was added to a solution of Fb-1e (14.5 mg, 19.8 μmol) in $CH_2Cl_2$/methanol (4 mL, 1:1). Standard workup and chromatography [silica, hexanes/$CH_2Cl_2$ (1:1)] gave a blue solid (13.4 mg, 85%): LD-MS obsd 790.33; FAB-MS obsd 791.1719, calcd 791.1672 ($C_{42}H_{41}CuIN_4$); $\lambda_{abs}$ 409 (log $\epsilon$=5.37), 510 (3.76), 604 (4.60) nm.

Cu(II)-5-(3,5-Di-tert-butylphenyl)-10-[4-[2-ethynyl]phenyl]-17,18-dyhydro-18,18-dimethyl-17-oxoporphyrin (Oxo-Cu-1d). A 25-fold excess of Cu(OAc)$_2 \cdot H_2O$ (115 mg, 0.575 mmol) was added to a solution of Oxo-Fb-1d (14.8 mg, 23.0 μmol) in $CH_2Cl_2$/methanol (5 mL, 1:1). Standard workup and chromatography [silica, hexanes/$CH_2Cl_2$ (1:1)] gave a blue solid (15.3 mg, 94%): LD-MS obsd 702.78; FAB-MS obsd 703.2512, calcd 703.2498 ($C_{44}H_{40}CuN_4O$); $\lambda_{abs}$ 420 (log $\epsilon$=5.41), 560 (3.88), 605 (4.55) mm.

Cu(II)-5-(3,5-Di-tert-butylphenyl)-17,18-Dihydro-10-(4-iodophenyl)-18,18-dimethyl-17-oxoporphyrin (Oxo-Cu-1e). A 25-fold excess of Cu(OAc)$_2 \cdot H_2O$ (115 mg, 0.575 mmol) was added to a solution of Oxo-Fb-1e (17.2 mg, 23.1 μmol) in $CH_2Cl_2$/methanol (5 mL, 1:1). Standard workup and chromatography [silica, hexanes/$CH_2Cl_2$ (1:1)] gave a blue solid (16.8 mg, 90%): LD-MS obsd 805.45; FAB-MS obsd 805.1486, calcd 805.1465 ($C_{42}H_{39}CuIN_4O$); $\lambda_{abs}$ 420 (log $\epsilon$=5.41), 560 (3.88), 605 (4.55) nm.

2-(2-Nitroethyl)pyrrole (2). Pyrrole-2-carboxaldehyde (2.85 g, 30.0 mmol) was dissolved in 90 mL of dry methanol and treated with nitromethane (4.85 mL, 90.0 mmol), sodium acetate (2.71 g, 33.0 mmol) and methylamine hydrochloride (2.23 g, 33.0 mmol). Stirring at room temperature for 12 h afforded a yellow/brown mixture. DMF (60 mL) and methanol (50 mL) were added to the reaction mixture. Sodium borohydride (3.97 g, 105 mmol) was added in portions. The reaction mixture was stirred at room temperature for 1 h, neutralized with acetic acid (5 mL) and evaporated. The mixture was dissolved in dichloromethane (150 mL), washed with water (50 mL×3) and dried with $Na_2SO_4$. The mixture was purified by column chromatography (silica, $CH_2Cl_2$) to give an orange oil (2.79 g, 66%). The $^1$H NMR spectrum and the $^1$H NMR spectrum were identical to the literature data (Strachan, J.-P. et al., *J. Org. Chem.* 2000, 65, 3160–3172): $^1$H NMR (400 MHz; CDCl$_3$) δ 3.31 (t, J=6.8 Hz, 2 H), 4.59 (t, J=6.8 Hz, 2 H), 5.99–6.01 (m, 1 H), 6.13–6.15 (m, 1 H), 6.69–6.71 (m, 1 H), 8.00–8.30 (br, 1 H); $^{13}$C NMR (100 MHz; CDCl$_3$) δ 25.4, 75.3, 106.9, 108.8, 117.8, 125.9; Anal. Calcd. for $C_6H_8N_2O_2$: C, 51.42; H, 5.75; N, 19.99. Found C, 51.38; H, 5.71; N, 19.92.

Compound 4. Following a general procedure (Strachan, J.-P. et al.,*J. Org. Chem.* 2000, 65, 3160–3172; Battersby, A. R. et al., *J. Chem. Soc. Perkin Trans.* 1 1984, 2725–2732), cesium fluoride (3.58 g, 23.6 mmol, 3.00 mol eq, freshly dried by heating to 100° C. under vacuum for 1 h and then cooling to room temperature under argon) was placed in a flask under argon. A mixture of 2 (1.10 g, 7.85 mmol) and ketone 3 (7.17 g, 47.1 mmol) (Fukuda, Y. et al., *Bull. Chem. Soc. Jpn.,* 1991, 64, 2013–2015) in 50 mL of dry acetonitrile was transferred to the flask by cannula. The mixture was heated at 70° C. for 7 h, whereupon the reaction was deemed to be complete by TLC analysis. The reaction mixture was filtered. The filtrate was evaporated and chromatographed [alumina, ethyl acetate/hexanes (1:3)], affording a light yellow oil which solidified upon storing in the freezer (1.11 g, 51%): mp 82° C.; $^1$H NMR (400 MHz; CDCl$_3$) δ 1.20–1.98 (m, 10H), 2.18 (s, 3H), 2.63, 2.70 (AB, $^2$J=17.7 Hz, 2H), 3.10 (ABX, $^3$J=2.7 Hz, $^2$J=15.3 Hz, 1H), 3.30 (ABX, $^3$J=11.7 Hz, $^2$J=15.3 Hz, 1H), 5.18 (ABX, $^3$J=2.7 Hz, $^3$J=11.7 Hz, 1H), 5.94–5.98 (m, 1H), 6.07–6.12 (m, 1H), 6.646.67 (m, 1H), 8.10–8.22 (br, 1H); $^{13}$C NMR (100 MHz; CDCl$_3$) δ 21.3, 25.3, 26.2, 30.9, 31.0, 32.2, 40.0, 43.8, 94.6, 107.1, 108.6, 117.7, 126.1, 207.7; Anal. Calcd. for $C_{15}H_{22}N_2O_3$: C, 64.73; H, 7.97; N, 10.06. Found C, 64.46; H, 7.88; N, 10.12.

Compound 5. Following a general procedure (Taniguchi, M. et al., *J. Org. Chem.* 2001, 66, 7342–7354), a vigorously stirred solution of 4 (700 mg, 2.51 mmol) in 12 mL of acetic acid and 12 mL of ethanol at 0° C. was treated with zinc dust (4.11 g, 62.8 mmol) in small portions over 5 min. The reaction mixture was stirred at 0° C. for 15 min, and then was filtered through Celite. The filtrate was concentrated under high vacuum. The resulting brown solid was purified by column chromatography [silica; packed and eluted with ethyl acetate/$CH_2Cl_2$ (1:1), then eluted with $CH_2Cl_2$/methanol (9:1)] affording a brown oil that solidified to brownish crystals on standing at room temperature (498 mg, 81%): mp 109–110° C.; $^1$H NMR δ 1.25–1.89 (m, 10 H), 2.01 (s, 3H), 2.28–2.44 (m, 2H), 3.00 (ABX, $^3$J=3.7 Hz, $^2$J=16.1 Hz, 1H), 3.17 (ABX, $^3$J=6.6 Hz, $^2$J=16.1 Hz, 1H), 3.83–3.91 (m, 1H), 5.92–5.96 (m, 1H), 6.04–6.09 (m, 1H), 6.66–6.71 (m, 1H), 10.35–10.60 (br, 1H); $^{13}$C NMR δ 13.2, 22.4, 25.6, 25.7, 30.8, 30.9, 37.0, 40.1, 42.8, 81.3, 106.4, 107.2, 117.3, 128.3, 146.1; FAB-MS obsd 247.1813, calcd 247.1810 ($C_{15}H_{22}N_2O$).

Compound 6. Following a procedure for the deoxygenation of tetrahydrodipyrrin N-oxides (Taniguchi, M. et al., *J. Org Chem.* 2001, 66, 7342–7354), TiCl$_4$ (1.51 mL, 13.7 mmol) was slowly added with stirring to dry THF (30 mL) under argon at 0° C. To the resulting yellow solution was slowly added LiAlH$_4$ (370 mg, 9.75 mmol). The resulting black mixture was stirred at room temperature for 15 min and then triethylamine (12.2 mL, 87.8 mmol) was added.

The black mixture was then poured into a solution of 4 (480 mg, 1.95 mmol) in dry THF (20 mL). The mixture was stirred for 30 min at room temperature and then water (25 mL) was added. The mixture was filtered. The filtrate was extracted with $CH_2Cl_2$. The organic layer was dried ($Na_2SO_4$) and evaporated under reduced pressure. The resulting yellow oil was purified by chromatography (silica, ethyl acetate) to give a pale yellow oil, which solidified to a pale yellow solid on cooling (228 mg, 51%): mp 54–55° C.; $^1$H NMR δ 1.16–1.71 (m, 10H), 2.04 (s, 3H), 2.31, 2.46 (AB, $^2$J=17.6 Hz, 2H), 2.53 (ABX, $^3$J=11.0 Hz, $^2$J=14.7 Hz, 1H), 2.85 (ABX, $^3$J=2.9 Hz, $^2$J=14.7 Hz, 1H), 3.63–3.73 (m, 1H), 5.92–5.96 (m, 1H), 6.08–6.13 (m, 1H), 6.68–6.73 (m, 1H), 9.70–9.95 (br, 1 H); $^{13}$C NMR δ 20.8, 23.6, 24.1, 26.4, 28.4, 31.3, 37.2, 45.9, 49.7, 81.1, 105.5,107.5, 116.6, 131.9, 174.2; FAB-MS obsd 231.1864, calcd 231.1861 (M+H) (M=$C_{18}H_{22}N_2O_5S$).

Zn-8. Following a general procedure for chlorin formation (Taniguchi, M. et al., *J. Org. Chem.* 2001, 66, 7342–7354), a solution of 7 (140 mg, 0.304 mmol) in 10 mL of anhydrous THF/methanol (4:1) was treated with a 10-fold excess of $NaBH_4$ (115 mg, 3.04 mmol). The reaction was monitored by TLC [silica, hexanes/ethyl acetate (5:1)] and upon completion was carefully quenched with cold water (50 mL), then extracted with distilled $CH_2Cl_2$ (3×20 mL). The combined organic layers were dried ($Na_2SO_4$) and concentrated under reduced pressure without heating to afford the carbinol 7-OH. The residue was dissolved in 3 mL of anhydrous $CH_3CN$. A sample of 6 (70.0 mg, 0.304 mmol) was added followed by TFA (23.4 μL, 0.304 mmol). The solution was stirred at room temperature for 30 min. The reaction was quenched with 10% aqueous $NaHCO_3$ (50 mL) and extracted with distilled $CH_2Cl_2$ (3×20 μL). The combined organic layers were washed with water, dried ($Na_2SO_4$) and concentrated in vacuo without heating. The residue, which contains the crude tetrahydrobilene-a, was dissolved in 30 mL of toluene, to which AgTf(137 mg, 0.534 mmol), $Zn(OAc)_2$ (490 mg, 2.67 mmol) and 2,2,6,6-tetramethylpiperidine (447 μL, 2.67 mmol) were added. The reaction mixture was refluxed for 24 h. The reaction mixture was concentrated and chromatographed [silica, hexanes/$CH_2Cl_2$ (2:1)] affording a blue solid (37 mg, 19%): $^1$H NMR δ 0.80–2.70 (m, 22H), 4.55 (s, 2H), 7.20 (s, 2H), 7.47 (d, J=8.1 Hz, 2H), 7.95 (d, J=8.1 Hz, 2H), 8.22 (d, J=4.5 Hz, 1H), 8.36 (d, J=4.5 Hz, 1H), 8.48 (d, J=4.5 Hz, 1H), 8.54–8.67 (m, 5H); LD-MS obsd 649.08, calcd 650.2388 ($C_{41}H_{38}N_4Zn$); $λ_{abs}$ 412, 610 nm; $λ_{em}$ 610, 654, 666 nm.

Oxo-Zn-8. A mixture of Zn-8 (25.0 mg, 38 μmol) and basic alumina (grade I, 1.70 g) in toluene (3 mL) was stirred at 85° C. for 15 h. The solvent was removed under reduced pressure and the alumina was washed ($CH_2Cl_2/CH_3OH$, 19:1) until the washings were colorless. The green solution was concentrated and dried under reduced pressure. The residue was dissolved in toluene (3 mL) and solid DDQ (16.9 mg, 76.1 μmol) was added. The mixture was stirred for 45 min. Triethylamine (300 μL) was added and the solvent was removed under reduced pressure. The residue was immediately chromatographed (silica, $CH_2Cl_2$), affording a green solid (5.0 mg, 20%): $^1$H NMR δ 0.85–2.70 (m, 22H), 7.23 (s, 2H), 7.51 (d, J=8.1 Hz, 2H), 7.98 (d, J=8.1 Hz, 2H), 8.22 (d, J=4.5 Hz, 1H), 8.45 (d, J=4.5 Hz, 1H), 8.53 (d, J=4.5 Hz, 1H), 8.80–8.93 (m, 3H), 8.98 (s, 1H), 9.45 (s, 1H); LD-MS obsd 664.70, calcd 664.2181 ($C_{41}H_{36}N_4OZn$); $λ_{abs}$ 424, 611 μm; $λ_{em}$ 611, 651, 669 μm.

17,18-Dihydro-15-iodo-10-mesityl-18,18-dimethyl-5-(4-methylphenyl)porphyrin (Fb-9). Following a general method for iodination of porphyrins (Shanmugathasan, S. et al., *J. Porphyrins Phthalocyanines* 2000, 4, 228–232), a solution of Fb-1a (51.5 mg, 93.9 μmol) in chloroform (45 mL) was treated with iodine (23.8 mg, 93.9 μmol), followed by pyridine (0.2 mL) and bis(trifluoroacetoxy)iodobenzene (40.4 mg, 93.9 μmol). The mixture was stirred for 20 min at room temperature. The solution was washed with aqueous $Na_2S_2O_3$ (2×50 mL), dried ($MgSO_4$), and filtered. The filtrate was concentrated under reduced pressure and the residue was purified by column chromatography [silica, hexanes/$CH_2Cl_2$ (2:1)] affording a dark pink solid (51.2 mg, 81%): $^1$H NMR δ −1.61−−1.53 (br, 1H), −1.37−−1.29 (br, 1H), 1.83 (s, 6H), 2.04 (s, 6H), 2.59 (s, 3H), 2.65 (s, 3H), 4.67 (s, 2H), 7.20–7.23 (m, 2H), 7.47–7.53 (m, 2H), 7.96–8.01 (m, 2H), 8.28 (d, J=4.5 Hz, 1H), 8.40 (d, J=4.5 Hz, 1H), 8.51 (dd, J=2.1 Hz, J=1.5 Hz, 1H), 8.71 (s, 1H), 8.74–8.79 (m, 2H), 9.07 (dd, J=1.5 Hz, J=2.1 Hz, 1H); LD-MS obsd 674.08; FAB-MS obsd 674.1912, calcd 674.1906 ($C_{38}H_{35}IN_4$); $λ_{abs}$ 414, 647 nm.

17,18-Dihydro-10-mesityl-18,18-dimethyl-5-(4-methylphenyl)-15-phenylporphyrin (Fb-11). Following a general method for Suzuki coupling (Zhou, X. et al., *J. Org. Chem.* 1998, 63, 99–104), Fb-9 (13.0 mg, 19.3 μmol), 10 (8.0 mg, 39.2 μmol), $Pd(PPh_3)_4$ (6.6 mg, 5.7 μmol, 30 mol %), and $K_2CO_3$ (21 mg, 0.15 mmol, 8.0 eq) were weighed into a Schlenk flask and the flask was pump-purged with argon three times. Toluene and DMF (2:1, 1.3 mL) were added and the mixture was heated for 17 h at 90° C. TLC analysis [silica, hexanes/$CH_2Cl_2$ (2:1)] showed three components. After removal of the solvent, $CH_2Cl_2$ (50 mL) was added and the mixture was filtered. The filtrate was concentrated and the residue was purified by column chromatography [silica, hexanes/$CH_2Cl_2$ (2:1)] affording a dark yellow solid, a fast-moving component (Pd-11) (2.1 mg, 15%) and a slow-moving component, Fb-11 (9.4 mg, 79%). Data for Pd-11: $^1$H NMR δ 1.83 (s, 6H), 1.92 (s, 6H), 2.56 (s, 3H), 2.65(s, 3H), 4.19 (s, 2H), 7.18 (s, 2H), 7.48 (d, J=7.8 Hz, 2H), 7.65 (m, 3H), 7.84 (m, 2H), 7.93 (d, J=8.1 Hz, 2H), 8.01 (d, J=5.1 Hz, 1H), 8.22 (d, J=4.8 Hz, 1H), 8.24 (d, J=5.1 Hz, 1H), 8.38 (d, J=4.8 Hz, 1H), 8.56 (d, J=4.8 Hz, 1H), 8.57 (d, J=4.5 Hz, 1H), 8.60 (s, 1H); LD-MS obsd 728.67; FAB-MS obsd 728.2166, calcd 728.2131 ($C_4H_{38}N_4Pd$); $λ_{abs}$ (toluene) 407, 595 nm. Data for Fb-11: $^1$H NMR δ −1.72 (br s, 1H), −1.48 (br s, 1H), 1.84 (s, 6H), 1.97 (s, 6H), 2.58 (s, 3H), 2.67(s. 3H), 4.18 (s, 2H), 7.21 (s, 2H), 7.51 (d, J=7.5 Hz, 2H), 7.70 (m, 3H), 7.92 (m, 2H), 8.03 (d, J=8.1 Hz, 2H), 8.19 (dd, J=4.5 Hz, J=0.9 Hz, 11H), 8.31 (d, J=4.2 Hz, l1H), 8.45 (d, J=4.2 Hz, 2H), 8.77 (d, J=4.5 Hz, 11H), 8.81 (d, J=4.5 Hz, 1H), 8.84 (s, 1H); LD-MS obsd 624.12; FAB-MS obsd 624.3274, calcd 624.3253 ($C_{44}H40N_4$); $λ_{abs}$ 418, 645 nm.

Zn(II)-17,18-Dihydro-10-mesityl-18,18-dimethyl-5-(4-methylphenyl)-15-phenylporphyrin (Zn-11). A solution of Fb-11 (25.2 mg, 40.3 μmol) in $CH_2Cl_2$ (10 mL) was treated with methanolic $Zn(OAc)_2$ (148 mg, 0.807 mmol) and the reaction mixture was stirred at room temperature for 2 h Standard workup and chromatography [silica, hexanes/$CH_2Cl_2$ (1:1)] gave a blue solid (22.8 mg, 82%): $^1$H NMR δ 1.85 (s, 6H), 1.94 (s, 6H), 2.56 (s, 3H), 2.66 (s, 3H), 4.50 (s, 2H), 7.18 (s, 2H), 7.48 (d, J=7.8 Hz, 2H), 7.65 (m, 3H), 7.87 (m, 211), 7.97 (d, J=7.8 Hz, 2H), 8.04 (d, J=4.8 Hz, 1H), 8.22 (d, J=4.5 Hz, 1H), 8.35 (d, J=4.8 Hz, 1H), 8.36 (d, J=4.2 Hz, 1H), 8.55 (s, 1H), 8.64 (d, J=4.5 Hz, 1H), 8.68 (d, J=4.5 Hz, 1H); LD-MS obsd 686.25; FAB-MS obsd 686.2377, calcd 686.2388 ($C_{44}H_{38}N_4Zn$); $λ_{abs}$ 416, 613 nm.

Zn(II)-17,18-Dihydro-17-hydroxy-10-mesityl-18,18-dimethyl-5-(4-methylphenyl)-15-phenylporphyrin (HO-Zn-11). A mixture of Zn-11 (6.9 mg, 10 μmol) and basic alumina (grade I, 1.1 g) in toluene (1.0 mL) was stirred for 40 h at 50° C. Solvent was removed under reduced pressure and the alumina was washed ($CH_2Cl_2$/methanol, 10:1) until the washings were colorless. The solution was concentrated and the residue was chromatographed (silica, $CH_2Cl_2$), affording HO-Zn-11 (6.1 mg, 87%): LD-MS obsd 700.04, calcd 702.2337 ($C_{44}H_{38}N_4OZn$).

Attempted oxidation of Zn(II)-17,18-dihydro-17-hydroxy-18,18-dimethyl-5-(4-methylphenyl)-10-mesityl-5-phenylporphyrin (HO-Zn-11). Following a general method for oxidation, a mixture of HO-Zn-11 and the oxidation reagent [DDQ, $MnO_2$, $Al_2O_3$, p-chloranil, or Al(t-BuO)$_3$] in toluene or methanol was stirred for several hours at room temperature or at elevated temperature. Solvent was removed under reduced pressure and the residue was purified by column chromatography (silica, $CH_2Cl_2$). In some cases the starting material was recovered unchanged (100%) while in others TLC analysis (silica, $CH_2Cl_2$) showed many spots.

Attempted oxidation of 17,18-dihydro-10-mesityl-18,18-dimethyl-5-(4-methylphenyl)-15-phenylporphyrin (Fb-11). A mixture of Fb-11 (9.9 mg, 16 μmol) and basic alumina (grade I, 1.6 g) in toluene (2.5 mL) was stirred for 40 h at 50° C. Solvent was removed under reduced pressure and the alumina was washed with $CH_2Cl_2$ (50 mL) until the washings were colorless. The solution was concentrated under reduced pressure. The starting material was recovered unchanged.

17,18-Dihydro-15-iodo-10-mesityl-18,18-dimethyl-5-(4-methylphenyl)-17-oxoporphyrin (Oxo-Fb-9). Following a general method for iodination of porphyrins, a solution of Oxo-Fb-1a (29.2 mg, 51.9 μmol) in $CHCl_3$ (20 mL) was treated with $I_2$ (13.2 mg, 52.0 μmol), followed by pyridine (70 μL) and bis(trifluoroacetoxy)iodobenzene (22.4 mg, 52.1 μmol). The mixture was stirred for 5 days at room temperature. TLC analysis [silica, hexanes/$CH_2Cl_2$ (1:1)] showed seven components. The solution was washed with aqueous $Na_2S_2O_3$ (2×70 mL), dried ($MgSO_4$), and filtered. The filtrate was concentrated and the residue was chromatographed [silica, hexanes/ethyl acetate (1:10)] to give fractions A and B. Fraction B was purified by chromatography [silica, hexanes/$CH_2Cl_2$ (1:1), three times; desired component had $R_f$=0.51 on TLC] to give a dark pink solid (8.0 mg, 22%): $^1$H NMR δ −1.77 (br s, 1H), −1.56 (br s, 1H), 1.83 (s, 6H), 2.07 (s, 6H), 2.62 (s, 3H), 2.68 (s, 3H), 7.25 (s, 2H), 7.54 (d, J=7.5 Hz, 2H), 8.02 (d, J=8.1 Hz, 2H), 8.41 (d, J=4.2 Hz, 1H), 8.49 (d, J=4.2 Hz, 1H), 8.64 (dd, J=2.1 Hz, J=2.4 Hz, 1H), 8.90 (dd, J=1.5 Hz, 1H), 9.01 (dd, J=1.8 Hz, 1H), 9.11(s, 1H), 9.65 (dd, J=2.1 Hz, 1H); LD-MS obsd 686.84; FAB-MS obsd 688.1725, calcd 688.1699 ($C_{38}H_{33}IN_4O$); $\lambda_{abs}$ 422, 649 nm.

17,18-Dihydro-18,18-dimethyl-5-(4-methylphenyl)-10-mesityl-17-oxo-15-phenylporphyrin (Oxo-Fb-11). Following a general method for Suzuki coupling, Oxo-Fb-9 (8.00 mg, 11.6 μmol), 10 (24.0 mg, 0.118 mmol), Pd(PPh$_3$)$_4$ (6.7 mg, 5.8 μmol, 50 mol %), and $K_2CO_3$ (12.85 mg, 92.96 μmol, 8.0 eq) were weighed into a Schlenk flask and the flask was pump-purged with argon three times. Toluene and DMF (2:1, 1.2 mL) were added and the mixture was heated for 20 h at 90° C. After removal of the solvent, $CH_2Cl_2$ (50 mL) was added and the mixture was filtered. The filtrate was concentrated under reduced pressure and the residue was purified by chromatography [silica, hexanes/$CH_2Cl_2$ (1:1)] to give a dark pink solid (4.8 mg, 65%): $^1$H NMR δ −1.97 (br s, 1H), −1.87 (br s, 1H), 1.83 (s, 6H), 2.00 (s, 6H), 2.60 (s, 3H), 2.69(s, 3H), 7.24 (s, 2H), 7.55 (d, J=7.8 Hz, 2H), 7.71 (m, 3H), 7.90 (m, 2H), 8.04 (d, J=7.8 Hz, 2H), 8.45 (d, J=4.8 Hz, 1H), 8.50 (dd, J=1.8 Hz, J=2.1 Hz, 1H), 8.54 (d, J=4.5 Hz, 1H), 8.56 (dd, J=1.8 Hz, 1H), 8.92 (d, J=4.5 Hz, 1H), 9.05 (d, J=3.9 Hz, 1H), 9.16 (s, 1H); LD-MS obsd 640.65; FAB-MS obsd 638.3052, calcd 638.3046 ($C_{44}H_{38}N_4O$); $\lambda_{abs}$ 417, 645 nm.

Zn(II)-17,18-Dihydro-18,18-dimethyl-5-(4-methylphenyl)-10-mesityl-17-oxo-15-phenylporphyrin (Oxo-Zn-11). A solution of Oxo-Fb-11 (3.2 mg, 5.0 μmol) in $CH_2Cl_2$ (8 mL) was treated with methanolic Zn(OAc)$_2$ (18.4 mg, 100 μmol) and the reaction mixture was stirred at room temperature for 22 h. Standard workup and chromatography (silica, $CH_2Cl_2$) gave a green solid (2.6 mg, 74%): $^1$H NMR δ 1.83 (s, 6H), 1.97 (s, 6H), 2.58 (s, 3H), 2.68 (s, 3H), 7.01 (s, 2H), 7.52 (d, J=8.1 Hz, 2H), 7.69 (m, 3H), 7.86 (m, 2H), 7.99 (d, J=7.8 Hz, 2H), 8.35 (d, J=4.5 Hz, 1H), 8.43 (d, J=4.2 Hz, 1H), 8.48 (d, J=4.5 Hz, 1H), 8.52 (d, J=4.2 Hz, 1H), 8.83 (d, J=4.2 Hz, 1H), 8.89 (d, J=4.8 Hz, 1H), 8.91 (s, 1H); LD-MS obsd 698.67; FAB-MS obsd 700.2178, calcd 700.2181 ($C_{44}H_{36}N_4Zn$); $\lambda_{abs}$ 425, 612 mn.

Zn(II)-17,18-Dihydro-15-iodo-10-mesityl-18,18-dimethyl-5-(4-methylphenyl)-porphyrin (Zn-9). A 20-fold excess of Zn(OAc)$_2$·2H$_2$O (277 mg, 1.26 mmol) was added to a solution of Fb-9 (42.5 mg, 63.0 μmol) in $CH_2Cl_2$ (20 mL) and methanol (2 mL). The metalation was complete in 3.5 h as confirmed by UV-vis and TLC analyses. Standard workup and chromatography [silica, $CH_2Cl_2$] gave a dark purple solid (28.7 mg, 62%): $^1$H NMR δ 1.84 (s, 6H), 2.01 (s, 6H), 2.57 (s, 3H), 2.65 (s, 3H), 4.61 (s, 2H), 7.17–7.20 (m, 2H), 7.45–7.49 (m, 2H), 7.90–7.94 (m, 2H), 8.18 (d, J=4.4 Hz, 1H), 8.30 (d, J=4.4 Hz, 1H), 8.40 (d, J=4.4 Hz, 1H), 8.41 (s, 1H), 8.58 (d, J=4.4 Hz, 1H), 8.64 (d, J=4.4 Hz, 1H), 9.02 (d, J=4.4 Hz, 1H); LD-MS obsd 736.35; FAB-MS obsd 736.1080, calcd 736.1041 ($C_{38}H_{33}IN_4Zn$); $\lambda_{abs}$ 419, 615 nm.

Zn(II)-15-Bromo-17,18-dihydro-10-mesityl-18,18-dimethyl-5-(4-methylphenyl)-porphyrin (Zn-12). Following a general method for bromination of porphyrins (Shi, X. et al., J. Org. Chem. 2000, 65, 1650–1664), a solution of Zn-1a (50.0 mg, 81.7 μmol) in THF (50 mL) was treated with NBS (14.5 mg, 81.7 μmol) and the reaction mixture was stirred at room temperature for 3 h. $CH_2Cl_2$ (100 mL) was added and the mixture was washed with aqueous NaHCO$_3$ (2×100 mL). The organic layer was dried (MgSO$_4$) and filtered. The filtrate was concentrated and the residue was chromatographed [silica, hexanes/$CH_2Cl_2$ (1:1)] to give a dark purple solid (45.8 mg, 81%): $^1$H NMR δ 1.84 (s, 6H), 2.02 (s, 6H), 2.57 (s, 3H), 2.65 (s, 3H), 4.56 (s, 2H), 7.17–7.20 (m, 2H), 7.47 (d, J=7.6 Hz, 2H), 7.92 (d, J=7.6 Hz, 2H), 8.20 (d, J=4.4 Hz, 1H), 8.31 (d, J=4.4 Hz, 1H), 8.44 (d, J=4.4 Hz, 1H), 8.46 (s, 1H), 8.59 (d, J=4.4 Hz, 1H), 8.64 (d, J=4.4 Hz, 1H), 8.99 (d, J=4.4 Hz, 1H); LD-MS obsd 688.33; FAB-MS obsd 688.1206, calcd 688.1180 ($C_{38}H_{33}BrN_4Zn$); $\lambda_{abs}$ 417, 614 nm.

Zn(II)-17,18-Dihydro-17-hydroxy-15-iodo-10-mesityl-18,18-dimethyl-5-(4-methylphenyl)porphyrin (HO-Zn-9). A mixture of Zn-9 (13.0 mg, 17.6 μmol) and basic alumina (grade I, 0.8 g) in toluene (1.0 mL) was stirred for 4 h at 50° C. The solvent was removed under reduced pressure and the alumina was washed ($CH_2Cl_2$/methanol, 10:1) until the washings were colorless. The washings were combined and concentrated. The resulting residue was chromatographed (silica, $CH_2Cl_2$), affording a blue-purple solid (8.7 mg, 66%): LD-MS obsd 752.32; FAB-MS obsd 753.1021, calcd 752.0991 ($C_{38}H_{33}IN_4OZn$); $\lambda_{abs}$ 419, 610 nm.

Attempted oxidation of Zn(II)-17,18-dihydro-17-hydroxy-15-iodo-10-mesityl-18,18-dimethyl-5-(4- methylphenyl)porphyrin (HO-Zn-9). Following our general method for oxidation, a mixture of HO-Zn-9 and DDQ was stirred in toluene for several hours at room temperature. The solvent was removed under reduced pressure and the residue was purified by column chromatography (silica, $CH_2Cl_2$). The starting material was recovered unchanged.

Zn(II)-15-Bromo-7,18-dihydro-17-hydroxy-10-mesityl-18,18-dimethyl-5-(4-methylphenyl)porphyrin (HO-Zn-12). A mixture of Zn-12 (13.5 mg, 19.5 µmol) and basic alumina (grade I, 0.8 g) in toluene (1.0 mL) was stirred for 4.5 h at 50° C. The solvent was removed under reduced pressure and the alumina was washed ($CH_2Cl_2$/methanol, 10:1) until the washings were colorless. The washings were combined and concentrated. The resulting residue was chromatographed (silica, $CH_2Cl_2$), affording a blue-purple solid (8.5 mg, 62%): LD-MS obsd 704.25 FAB-MS obsd 704.1147, calcd 704.1129 ($C_{38}H_{33}BrN_4OZn$); $\lambda_{abs}$ 416, 608 nm.

Attempted oxidation of Zn(II)-15-bromo-17,18-dihydro-17-hydroxy-10-mesityl-18,18-dimethyl-5-(4-methylphenyl) porphyrin (HO-Zn-12). Following our general method for oxidation, a mixture of HO-Zn-12 and DDQ was stirred in toluene for several hours at room temperature. The solvent was removed under reduced pressure and the residue was purified by column chromatography (silica, $CH_2Cl_2$). The starting material was recovered unchanged.

Zn(II)-20-Bromo-17,18-dihydro-10-mesityl-18,18-dimethyl-5-(4-methylphenyl)-17-oxoporphyrin (Oxo-Zn-13). Following a general method for bromination of porphyrins (Shi, X. et al., *J. Org. Chem.* 2000, 65, 1650–1664), a solution of Oxo-Zn-1a (10.0 mg, 16.0 µmol) in THF (10 mL) was treated with NBS (2.84 mg, 16.0 µmol) and the reaction mixture was stirred at room temperature for 40 min. $CH_2Cl_2$ (50 mL) was added and the mixture was washed with aqueous $NaHCO_3$ (2×50 mL). The organic layer was dried ($MgSO_4$) and filtered. The filtrate was concentrated and the residue was chromatographed [silica, hexanes/$CH_2Cl_2$ (3:1)] to give a dark purple solid (8.7 mg, 77%): $^1$H NMR δ 1.82 (s, 6H), 2.17 (s, 6H), 2.60 (s, 3H), 2.68 (s, 3H), 7.20–7.24 (m, 2H), 7.50 (d, J=8.0 Hz, 2H), 7.95 (d, J=8.0 Hz, 2H), 8.43 (d, J=4.4 Hz, 1H), 8.51 (d, J=4.4 Hz, 1H), 8.64 (d, J=4.4 Hz, 1H), 8.76 (d, J=4.4 Hz, 1H), 8.91 (d, J=4.4 Hz, 1H), 9.46 (d, J=4.4 Hz, 1H), 9.50 (s, 1H); LD-MS obsd 700.96; FAB-MS obsd 702.0959, calcd 702.0973 ($C_{38}H_{31}BrN_4OZn$); $\lambda_{abs}$ 429, 615 nm.

Zn(II)-17,18-Dihydro-10-mesityl-18,18-dimethyl-5-(4-methylphenyl)-17-oxo-20-phenylporphyrin (Oxo-Zn-14). Following a general method for Suzuki coupling (Zhou, X. et al., *J. Org. Chem.* 1998, 63, 99–104), Oxo-Zn-13 (6.8 mg, 9.6 µmol), 10 (9.8 mg, 48 µmol), Pd(PPh$_3$)$_4$ (3.4 mg, 9.0 µmol, 30 mol %), and $K_2CO_3$ (11 mg, 77 µmol, 8.0 eq) were weighed into a Schlenk flask and the flask was pump-purged with argon three times. Toluene and DMF (2:1, 1 mL) were added and the mixture was heated for 17 h at 90° C. TLC analysis [silica, hexanes/$CH_2Cl_2$ (2:1)] showed two components. After removal of the solvent, $CH_2Cl_2$ (50 mL) was added and the mixture was washed with aqueous $NaHCO_3$ (2×50 mL). The organic layer was dried ($MgSO_4$) and filtered. The filtrate was concentrated and the residue was chromatographed [silica, hexanes/$CH_2Cl_2$ (1:3)] to give a fast-moving component (Oxo-Zn-14, 3.2 mg, 46%) and a slow-moving component (Oxo-Zn-1a, 1.3 mg, 21%). Data for Oxo-Zn-14: $^1$H NMR δ 1.68 (s, 6H), 1.84 (s, 6H), 2.61 (s, 3H), 2.66 (s, 3H), 7.22–7.25 (m, 2H), 7.46–7.49 (m, 2H), 7.63–7.67 (m, 2H), 7.70–7.74 (m, 1H), 7.91–7.94 (m, 2H), 7.94–7.97 (m, 2H), 8.10–8.12 (m, 2H), 8.11 (d, J=4.4 Hz, 1H), 8.46 (d, J=4.4 Hz, 1H), 8.53 (d, J=4.4 Hz, 1H), 8.62 (d, J=4.4 Hz, 1H), 8.68 (d, J=4.4 Hz, 1H), 8.96 (d, J=4.4 Hz, 1H), 9.65 (s, 1H); LD-MS obsd 699.13; FAB-MS obsd 700.2182, calcd 700.2181 ($C_{44}H_{36}N_4OZn$); $\lambda_{abs}$ 427, 614 nm.

ZnFb-dyad. Following the refined Pd-mediated coupling procedure (Wagner, R. W. et al., *Chem. Mater.* 1999, 11, 2974–2983), samples of Zn-1d (26.5 mg, 38.3 µmol), Fb-1e (28.0 mg, 38.3 µmol), Pd$_2$(dba)$_3$ (5.26 mg, 5.75 µmol), and P(o-tol)$_3$ (14.0 mg, 46.0 µmol) were weighed into a 100-mL Schlenk flask which was then pump-purged three times with argon. Toluene/triethylamine (5:1, 15 mL) was added and the flask was stirred at 35° C. Analytical SEC showed that the reaction had leveled off after 5 h. The solvent was removed and the residue was chromatographed (silica, toluene) affording unreacted chlorin monomers followed by the desired dyad and then high molecular weight material (HMWM). The mixture of dyad and HMWM was concentrated to dryness, dissolved in THF, and chromatographed in four equal portions (SEC, THF). Gravity elution afforded dimer-containing fractions. The dyad-containing fractions were combined and chromatographed (silica, toluene), affording a bluish purple solid (11.3 mg, 23%): $^1$H NMR (toluene-d$_8$) δ −1.39−−1.37 (br, 2H), 1.50 (s, 18H), 1.54 (s, 18H), 1.92 (s, 6H), 1.93 (s, 6H), 4.16 (s, 2H), 4.29 (s, 2H), 7.92–7.96 (m, 4H), 7.97–8.03 (m, 4H), 8.11–8.15 (m, 2H), 8.22 (d, J=2.0 Hz, 2H), 8.29 (d, J=2.0 Hz, 2H), 8.43 (1H, s), 8.45 (1H, s), 8.56–8.63 (m, 5H), 8.69–8.76 (m, 4H), 8.79–8.81 (m, 1H), 8.83–8.86 (m, 2H), 8.94–8.97 (m, 2H); LD-MS obsd 1293.18, calcd 1292.6110 ($C_{86}H_{84}N_8Zn$); $\lambda_{abs}$ 415 (log ε=5.44), 510 (4.24), 609 (4.55), 641 (4.47) nm; $\lambda_{em}$ 611, 641, 683, 708 nm ($\Phi_f$=0.22).

Zn$_2$-dyad. Following the procedure described for the preparation of ZnFb-dyad, samples of Zn-1d (13.8 mg, 20.0 µmol) and Zn-1e (15.9 mg, 20.0 µmol) were coupled using Pd$_2$(dba)$_3$ (2.75 mg, 3.00 µmol) and P(o-tol) (7.31 mg, 24.0 mol) in toluene/triethylamine (5:1, 8 mL) at 35° C. under argon. After 1.5 h, Pd$_2$(dba)$_3$ (2.75 mg, 3.00 µmol) and P(o-tol)$_3$ (7.31 mg, 24.0 µmol) were added to the reaction mixture. Analytical SEC showed that the reaction had leveled off after 2.5 h. Chromatography (silica, toluene) removed the Pd species and afforded a mixture of chlorins. Further chromatography in four equal portions (SEC, THF) afforded dyad-containing fractions. The dyad-containing fractions were combined and chromatographed (silica, toluene), affording a bluish purple solid (8.3 mg, 31%): $^1$H NMR (toluene-d$_8$) δ 1.53 (s, 36H), 1.87 (s, 12H), 4.16 (s, 4H), 7.92–7.95 (m, 2H), 7.99 (d, J=8.0 Hz, 4H), 8.13 (d, J=8.0 Hz, 4H), 8.27–8.29 (m, 4H), 8.42 (s, 2H), 8.45 (s, 2H), 8.55–8.60 (m, 6H), 8.73 (d, J=4.4 Hz, 2H), 8.84 (d, J=4.4 Hz, 2H), 8.95 (d, J=4.4 Hz, 2H); LD-MS obsd 1354.03; calcd 1354.5245 ($C_{86}H_{82}N_8Zn_2$); FAB-MS: High resolution mass spectrometry was carried out on this sample at greater than unit resolution. Signal-to-noise levels were not sufficient to allow measurement of the nominal exact mass ion, but the base peak in the isotope cluster was observed at 1358.5221 (calcd 1358.5230), thus, elemental composition was confirmed as $C_{86}H_{82}N_8Zn_2$; $\lambda_{abs}$ 415 (log ε=5.54), 563 (3.45), 609 (4.91) nm; $\lambda_{em}$ 611, 666 nm ($\Phi_f$=0.053).

Cu$_2$-dimer. Following the procedure described for the preparation of ZnFb-dyad, samples of Cu-1d (8.70 mg, 12.6 µmol) and Cu-1e (10.0 mg, 12.6 µmol) were coupled using Pd$_2$(dba)$_3$ (1.73 mg, 1.89 µmol) and P(o-tol)$_3$ (4.60 mg, 15.1 µmol) in toluene/triethylamine (5:1, 5 mL) at 35° C. under argon. Analytical SEC showed that the reaction had leveled off after 2.5 h. Chromatography (silica, toluene) removed the Pd species and afforded a mixture of chlorins. Further chromatography in two equal portions (SEC, toluene) afforded dimer-containing fractions. The dimer-containing fractions were combined and chromatographed (silica, ethyl acetate), affording a blue solid (4.3 mg, 25%): LD-MS obsd 1355.41, calcd 1352.5454 ($C_{86}H_{82}Cu_2N_8$); kabs 411 (log ε=5.23), 500 (3.83), 605 (4.53) nm.

ZnFb-Oxo-dyad. Following the procedure described for the preparation of ZnFb-dyad, samples of Oxo-Zn-1d (28.7 mg, 40.6 μmol) and Oxo-Fb-1e (30.2 mg, 40.6 μmol), were coupled using $Pd_2(dba)_3$ (5.57 mg, 6.08 μmol) and $P(o\text{-tol})_3$ (14.8 mg, 48.7 μmol) in toluene/triethylamine (5:1, 16 mL) at 35° C. under argon. After 3.5 h, $Pd_2(dba)_3$ (5.57 mg, 6.08 μmol) and $P(o\text{-tol})_3$ (14.8 mg, 48.7 μmol) were added to the reaction mixture. Analytical SEC showed that the reaction had leveled off after 4.5 h. Chromatography (silica, $CH_2Cl_2$) removed the Pd species and afforded a mixture of chlorins. Further chromatography in three equal portions (SEC, THF) afforded dyad-containing fractions. The dyad-containing fractions were combined and chromatographed (silica, $CH_2Cl_2$), affording a bluish purple solid (27.8 mg, 52%): $^1$H NMR (toluene-$d_8$) δ −2.36−−2.33 (br, 1H), −2.22−−2.19 (br, 1H), 1.52 (s, 18H), 1.54 (s, 18H), 2.06 (s, 6H), 2.06 (s, 6H), 7.78−7.82 (m, 2H), 7.97−8.02 (m, 4H), 8.02−8.07 (m, 4H), 8.17−8.20 (m, 2H), 8.22−8.26 (m, 2H), 8.67−8.72 (m, 4H), 8.87−8.91 (m, 2H), 8.95−8.97 (m, 1H), 8.97−8.98 (m, 2H), 8.99 (1H, s), 9.10−9.12 (m, 1H), 9.19−9.21 (m, 1H), 9.23 (s, 1H), 9.61 (s, 1H), 9.77 (s, 1H); LD-MS obsd 1320.78; FAB-MS: High resolution mass spectroscopy was carried out on this sample at greater than unit resolution and the expected molecule ion was observed at m/z 1320.56 (calcd 1320.57), thus, elemental composition was confirmed as $C_{86}H_{80}N_8O_2Zn$; $\lambda_{abs}$ 425 (log ε=5.73), 514 (4.31), 549 (4.24), 594 (4.22), 610 (4.74), 643 (4.31) nm; $\lambda_{em}$ 641, 683, 707 nm ($\Phi_f$=0.29).

$Zn_2$-Oxo-dyad. A 50-fold excess of $Zn(OAc)_2 \cdot 2H_2O$ (100 mg, 0.454 mmol) was added to a solution of ZnFb-Oxo-dyad (12.0 mg, 9.07 μmol) in $CH_2Cl_2$ (10 mL) and methanol (1 mL). The metalation was complete in 14 h as confirmed by UV-Vis and TLC analyses. Standard workup and chromatography [silica, $CH_2Cl_2$-hexane (1:1), ethyl acetate] gave a bluish purple solid (4.25 mg, 34%): $^1$H NMR (toluene-$d_8$) δ 1.53 (s, 36H), 2.06 (s, 12H), 7.93−7.95 (m, 2H), 7.98 (d, J=8.0 Hz, 4H), 8.09 (d, J=8.0 Hz, 4H), 8.26−8.27 (m, 4H), 8.66 (s, 2H), 8.69−8.72 (m, 4H), 8.75 (d, J=4.8 Hz, 2H), 8.82−8.85 (m, 4H), 9.03 (d, J=4.8 Hz, 2H), 9.76 (s, 2H); LD-MS obsd 1382.16, calcd 1382.4831 ($C_{86}H_{78}N_8O_2Zn$); $\lambda_{abs}$ 428, 563, 610 nm; $\lambda_{em}$ 609, 666 nm ($\Phi_f$=0.065).

$Cu_2$-Oxo-dimer. Following the procedure described for the preparation of ZnFb-dyad, samples of Oxo-Cu-1d (8.70 mg, 12.4 μmol) and Oxo-Cu-1e (10.0 mg, 12.4 lmol) were coupled using $Pd_2(dba)_3$ (1.70 mg, 1.86 μmol) and $P(o\text{-tol})_3$ (4.53 mg, 14.9 μmol) in tolueneltriethylamine (5:1, 5 mL) at 35° C. under argon. After 2.5 h, $Pd_2(dba)_3$ (1.70 mg, 1.86 μmol) and $P(o\text{-tol})_3$ (4.53 mg, 14.9 μmol) were added to the reaction mixture. Analytical SEC showed that the reaction had leveled off after 3.5 h. Chromatography (silica, toluene) removed the Pd species and afforded a mixture of chlorins. Further chromatography in two equal portions (SEC, THF) afforded dimer-containing fractions. The dimer-containing fractions were combined and chromatographed (silica, toluene), affording a blue solid (11.6 mg, 68%): LD-MS obsd 1382.36, calcd 1380.5040 ($C_{86}H_{78}Cu_2N_8O_2$); $\lambda_{abs}$ 424 (log ε=5.68), 561 (4.21), 605 (4.83) nm.

EXAMPLE 2

Synthesis of Oxochlorins

Conversion of chlorins to oxochlorins. Zn-chlorins Zn-1a,b were readily available for use in these studies (Scheme 1) (Strachan, J.-P. et al., *J. Org. Chem.* 2000,

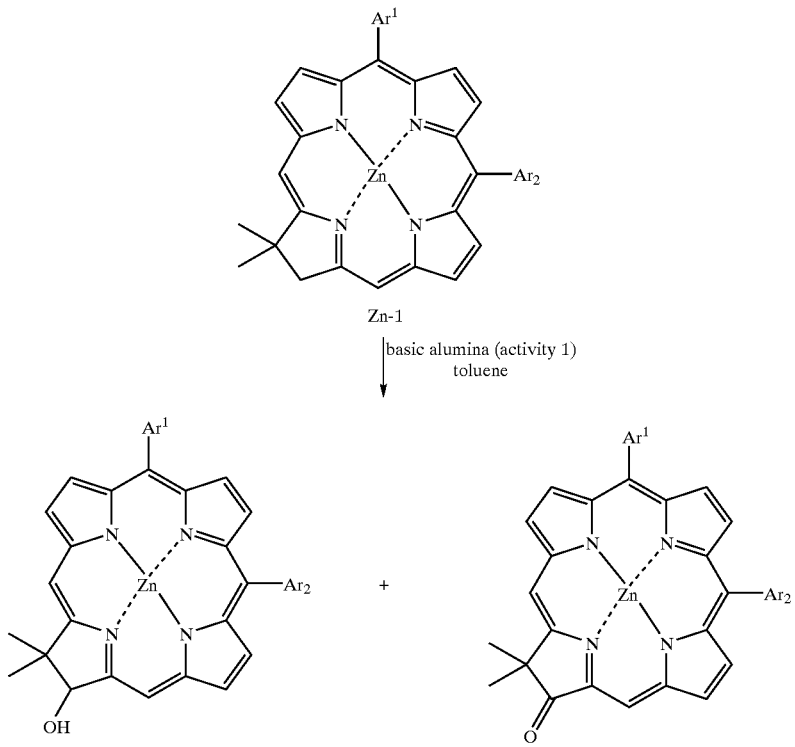

Scheme 1

-continued

HO-Zn-1 　　　　　　　　　　　　　　　Oxo-Zn-1

DDQ
toluene

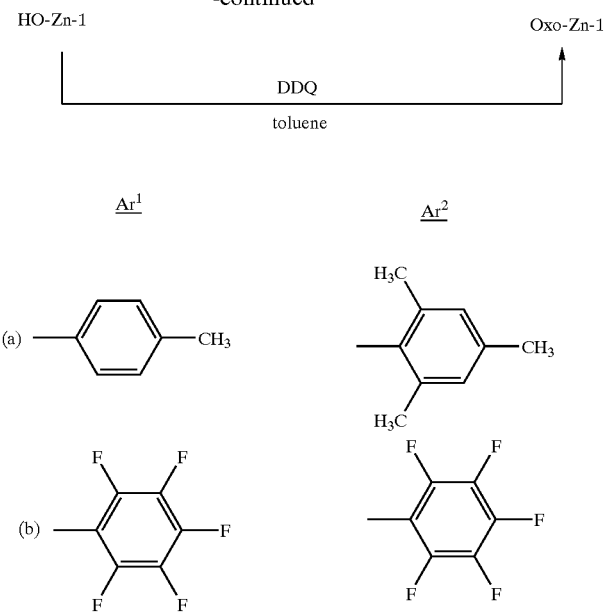

65, 3160–3172; Taniguchi, M. et al., *J. Org. Chem.* 2001, 66, 7342–7354). We first examined several reagents known for the oxidation of the benzylic methylene unit to the corresponding carbonyl or hydroxy groups, including $MnO_2$, $CrO_3$, $Cu(OAc)_2$, and $SeO_2$. While most of these reagents are employed at high concentration and/or at elevated temperatures, we screened these reagents at room temperature in dilute solution owing to the constraints of solubility and chemical sensitivity with porphyrinic macrocycles. Treatment of Zn-1a with $MnO_2$, $Cu(OAc)_2$ or $SeO_2$ proved ineffective, while $CrO_3$ led to extensive decomposition. Given the facile hydroxylation of certain chlorins during chromatography on neutral alumina (Burns, D. H. et al., *Chem. Commun.* 1998, 1677–1678), we decided to explore this side-reaction as the first step in a procedure for converting chlorins to oxochlorins. Thus, a mixture of Zn-1a and basic alumina (activity I) in toluene at room temperature was stirred in a reaction vessel exposed to air for 36 h. Elution of the chlorin species and analysis by TLC showed three components: a fast-moving blue component ($R_f$=0.82), a medium-fast moving green component (Rf=0.38), and a slow-moving blue component ($R_f$=0.15). LD-MS analysis of the components revealed their identity as unchanged starting material (Zn-1a), oxochlorin Oxo-Zn-1a and hydroxychlorin HO-Zn-1a. The three components were easily separated by column chromatography on silica. (The same reaction in dichloromethane proved inefficient, presumably due to poorer adsorption of the chlorin on alumina in this more polar solvent.) Similar results were obtained with Zn-1b though oxidation was slower in this case. However, our attempts to convert Fb-1a,b to the corresponding hydroxychlorins were not successful; unchanged starting material was recovered in near-quantitative amounts in each case.

To identify the grade and nature of alumina for the oxidation, experiments were done in parallel employing basic alumina (activity I), neutral alumina, and basic alumina (activity V). In each case, a mixture of chlorin (1 mg) and alumina (70 mg) in toluene (0.4 mL) was stirred for 14 h in a vial loosely plugged with cotton. The reaction was most efficient on the most active grade of alumina. A small amount of oxochlorin was formed in each case.

Given the facile formation of the hydroxychlorins, their conversion to the corresponding oxochlorins was investigated. Several reagents are available for the oxidation of secondary alcohols to ketones. No reaction was obtained with $SeO_2$ or p-chloranil with hydroxychlorin HO-Zn-1a under room-temperature conditions. $MnO_2$ was an efficient oxidizing agent for reactions on a small scale, but gave erratic results upon scale-up. Moreover, the prolonged reaction time (>96 h) made this reagent less attractive. The reaction with DDQ in dichloromethane led to decomposition. However, the oxidation with ~2–3 equivalents of DDQ in toluene proceeded rapidly with few side reactions. When the reaction was carried out on a 10 mg-scale, oxochlorin Oxo-Zn-1a was obtained in 90% yield, while the synthesis at the preparative level gave Oxo-Zn-1a in 55% yield. Similar results were achieved in the conversion of HO-Zn-1b to Oxo-Zn-1b (74% yield). The structure of each oxochlorin product was assigned on the basis of $^1H$ NMR and LD-MS data.

In an attempt to shorten reaction times and simplify work-up procedures, oxidation of Zn-1a with alumina was attempted at 50° C. for 15 h, whereupon the starting material was completely consumed yielding a mixture of HO-Zn-1a and Oxo-Zn-1a. Oxidation of the mixture with DDQ afforded Oxo-Zn-1a in 54% yield.

The efficiency of DDQ-oxidation is a sensitive function of concentration of hydroxychlorin. Higher yields of oxochlorin were obtained when the oxidation was carried out in dilute solutions (10 mM). At higher concentration (>40 mM), substantial decomposition of chlorins to base-line material was observed.

A one-flask conversion of chlorins to oxochlorins was attempted by using excess DDQ (6 equivalents) in toluene as the oxidizing agent in the absence of alumina. The oxochlorin was formed rapidly. The oxochlorin was isolated in 50% yield but the chromatographic separation was more difficult than the two-step alumina-DDQ procedure owing to the formation of unwanted side products.

The demetalation of Oxo-Zn-1a,b was achieved using TFA in $CH_2Cl_2$, affording the corresponding free base oxochlorin Oxo-Fb-1a,b. Treatment of oxochlorin Oxo-Fb-1a to the heterogeneous magnesium insertion procedure ($MgI_2$, DIEA, $CH_2Cl_2$) (Lindsey, J. S. et al., *Inorg. Chem.* 1995, 34, 1063–1069) afforded the corresponding magnesium chelate Oxo-Mg-1a. In contrast to Mg-1a, which is readily demetalated upon workup, magnesium oxochlorin Oxo-Mg-1a is relatively stable and could be purified by chromatography over basic alumina (activity V). For resonance Raman studies, copper chelates Cu-1a,b and Oxo-Cu-1a,b were prepared. It is interesting to note that attempts to convert Cu-1a to the hydroxychlorin by exposure to alumina were unsuccessful and the parent chlorin was obtained unchanged. When DDQ alone was used as the oxidizing agent, extensive decomposition was observed with formation of a small amount of Oxo-Cu-1a (<10%).

New substituted chlorins and oxochlorins.

(a) Chlorins/oxochlorins for surface attachment. Chlorins bearing suitable functional groups can be attached to a surface. Chlorins bound to metal oxide surfaces ($TiO_2$, $SnO_2$, etc.) can be used in studies of photoinduced electron-transfer processes. Carboxy groups provide ideal attachment moieties for binding to metal oxide surfaces. A chlorin bearing a single carboxy substituent (Zn-1c) was prepared. For comparative studies of chlorins and oxochlorins bound to a surface, we sought the oxochlorin analog of Zn-1c. Thus, the two-step oxidation of chlorin Zn-1c gave the corresponding oxochlorin Oxo-Zn-1c in 31% yield (Scheme 2).

(b) Chlorin/oxochlorin building blocks. Meso-substituted chlorins bearing an iodo group or an ethynyl group were synthesized via tetrahydrobilene-a intermediates (Taniguchi, M. et al., *J. Org. Chem.* 2001, 66, 7342–7354). These chlorins incorporate the 3,5-di-tert-butyl phenyl group for increased solubility in organic solvents. The initial attempt to synthesize chlorin-chlorin dyads bearing para-tolyl groups was not successful due to the lower solubility of these compounds in organic solvents.

Zinc oxochlorins were readily obtained by the oxidation of the corresponding zinc chlorins in the same manner (alumina/DDQ) as described above. The zinc chlorin (Zn-1d or Zn-1e) was treated with basic alumina in toluene at 50° C. (Scheme 3). After 5–8 h, TLC analysis showed that the zinc chlorin was consumed and two new spots corresponding to the oxochlorin (Oxo-Zn-1d or Oxo-Zn-1e) (minor spot) and the hydroxychlorin (major spot) appeared. The reaction mixture was treated with DDQ to convert the hydroxychlorin to the oxochlorin. The reaction was fast; after 1 min all the hydroxychlorin was converted into the oxochlorin. In this manner, oxochlorins Oxo-Zn-1d and Oxo-Zn-1e were isolated in 60–65% yields.

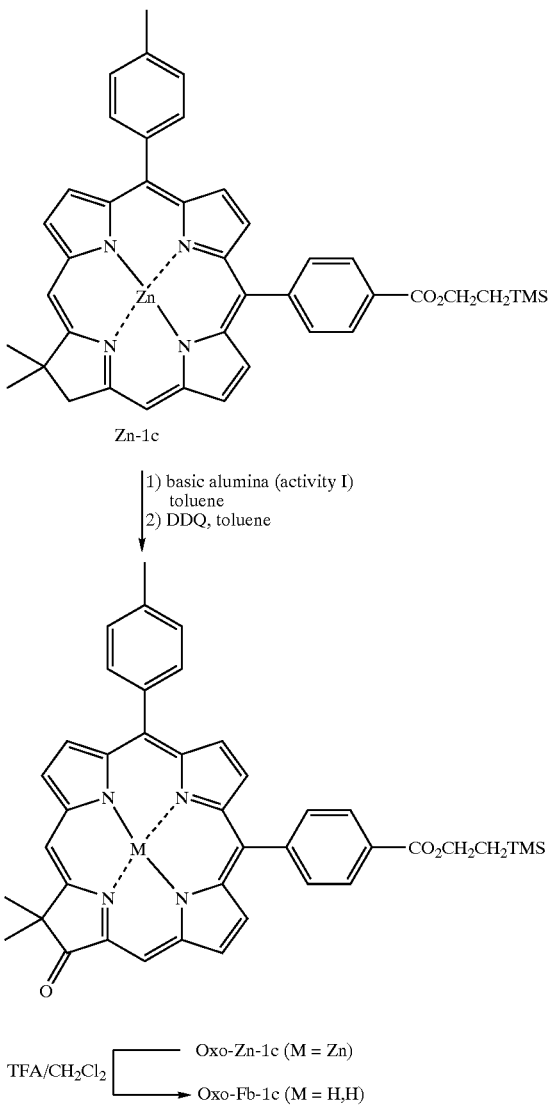

Scheme 2

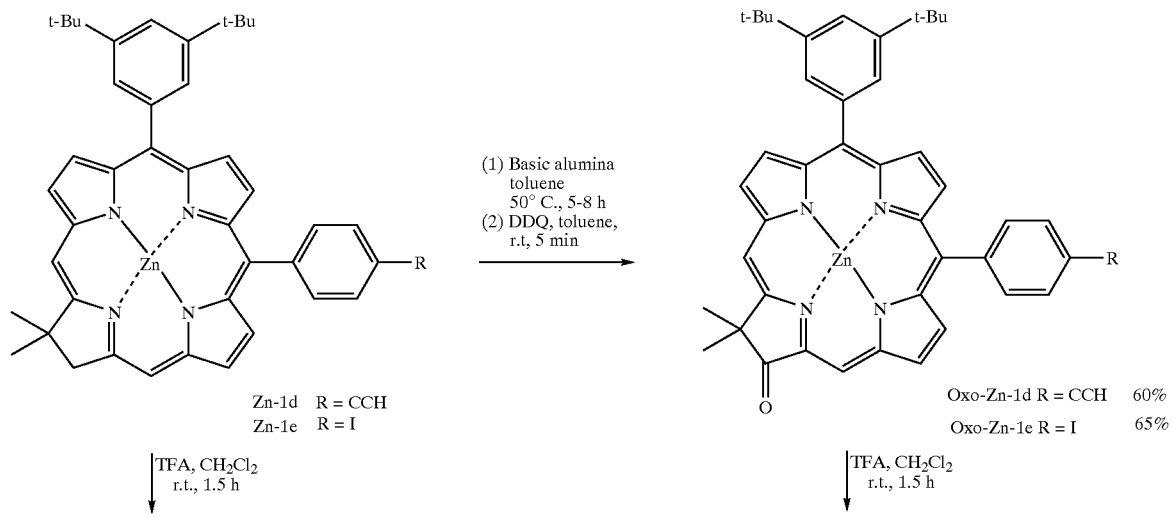

Scheme 3

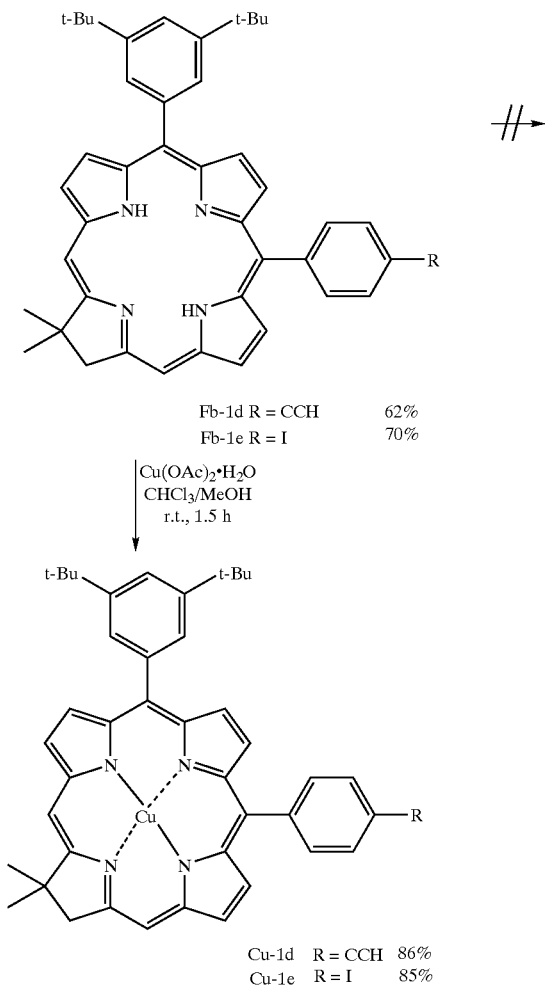

Fb-1d R = CCH  62%
Fb-1e R = I  70%

Cu(OAc)₂·H₂O
CHCl₃/MeOH
r.t., 1.5 h

Cu-1d  R = CCH  86%
Cu-1e  R = I  85%

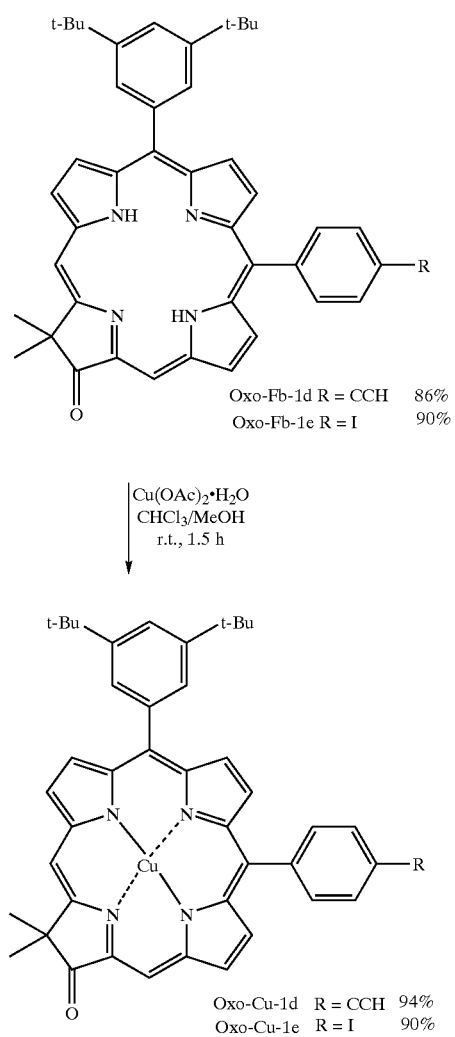

Oxo-Fb-1d R = CCH  86%
Oxo-Fb-1e R = I  90%

Cu(OAc)₂·H₂O
CHCl₃/MeOH
r.t., 1.5 h

Oxo-Cu-1d  R = CCH  94%
Oxo-Cu-1e  R = I  90%

The free base chlorins Fb-1d,e and oxochlorins Oxo-Fb-1d,e were obtained by demetalation of the corresponding zinc chlorins Zn-1d,e and zinc oxochlorins Oxo-Zn-1d,e with TFA in $CH_2Cl_2$. All attempts to make free base oxochlorins via oxidation of free base chlorins were not successful.

The copper chelates of chlorins (Cu-1d,e) and oxochlorins (Oxo-Cu-1d,e) were prepared by treating the corresponding free base chlorins Fb-1d,e and oxochlorins Oxo-Fb-1d,e with $Cu(OAc)_2$ in $CH_2Cl_2$/methanol (1:1) at room temperature.

(c) Spiro-chlorins/oxochlorins. The existing methodology for preparing chlorin/oxochlorin building blocks is well suited for introducing substituents at the 5 and 10-positions. For many applications, the availability of only two sites of substitution is rather limiting. By contrast, the four meso-sites in porphyrins are readily available for incorporation of diverse substituents. While typically two sites are used as synthetic handles, the remaining two can be used to achieve the desired solubility properties. With chlorins we sought to introduce groups at sites other than the 5,10-positions to achieve the desired solubility or to introduce other synthetic handles.

The incorporation of longer alkyl chains at the 18-position can be achieved by the modification of the chlorin-forming reaction that was reported earlier (Taniguchi, M. et al., J. Org. Chem. 2001, 66, 7342–7354). The synthesis of the requisite Western half begins with pyrrole-2-carboxaldehyde and proceeds to nitroethyl pyrrole 2. The prior synthesis of 2 was achieved in somewhat low yield by formation of the nitrovinyl pyrrole intermediate which is then reduced with $NaBH_4$. To achieve an increased yield of the critical intermediate 2, a two-step, one-flask synthesis of 2 without isolation of the intermediate nitrovinyl pyrrole (Strachan, J.-P. et al., J. Org. Chem. 2000, 65, 3160–3172) was developed. This procedure involves a much simpler workup procedure and affords 2 in slightly greater yield than the two-step procedure (51% versus 45% yield).

A key step in the synthesis of the desired C-alkylated chlorins is the Michael addition of nitroethyl pyrrole 2 to suitable α,β-unsaturated ketones having long alkyl chains as β-substituents. These, in principle, are readily accessible from the corresponding ketones via a Wittig-Horner reaction. Higher homologues (C9 or higher) of linear aliphatic ketones screened by us were unreactive under these conditions. However, cyclohexanone reacted smoothly with dimethyl (2-oxopropyl)phosphonate to yield the corresponding α,β-unsaturated ketone 3. Reaction of the latter with nitroethyl pyrrole 2 under the standard conditions gave the corresponding tetrahydrodipyrrin 6 (Scheme 4).

Scheme 4

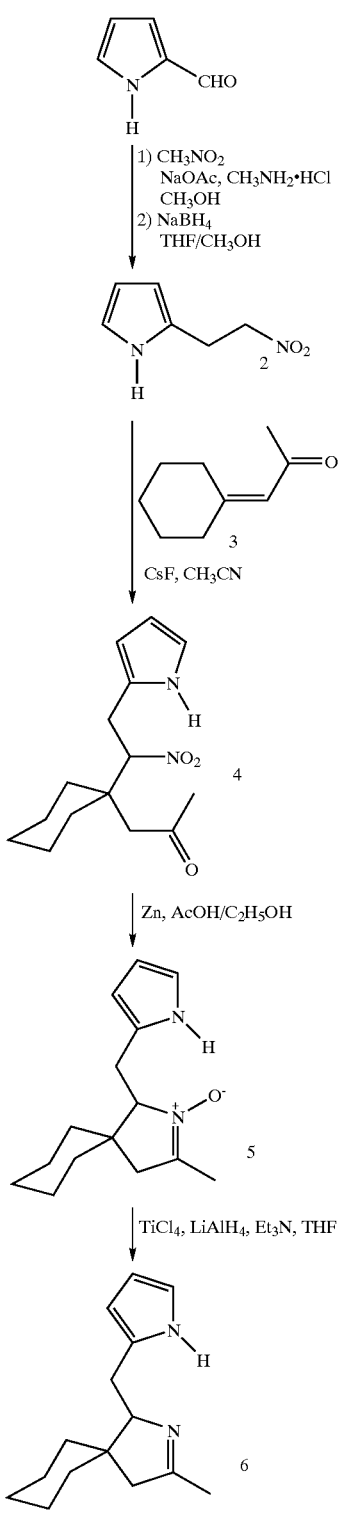

Treatment of 6 to the two-step chlorin-forming conditions developed earlier gave the chlorin Zn-8. Oxidation of Zn-8 under the conditions described above (alumina/DDQ) led to the corresponding oxochlorin Oxo-Zn-8 (Scheme 5).

(d) Trans-substituted chlorins/oxochlorins. The incorporation of chlorins or oxochlorins as integral units in linear multi-pigment arrays requires access to trans-substituted chlorin or oxochlorin building blocks. We previously have prepared chlorins bearing substituents at the 2,12-positions, which entailed lengthy synthesis beginning with the preparation of β-substituted pyrroles. The synthesis of meso-substituted chlorins entails much less synthesis, but heretofore the only accessible meso-substituted chlorins have had substituents at the 5- and 10-positions. The ability to introduce a substituent at the 15- or 20-position would provide facile access to trans-substituted building blocks of chlorins and oxochlorins.

The formation of trans-substituted oxochlorins involves these three steps; (1) meso-halogenation, (2) substitution of the meso-halogen group by metal-mediated coupling (e.g., Suzuki or Sonogashira reactions), (3) oxidation of the 17-position (conversion of the chlorin to the oxochlorin). There are three possible strategies by changing the sequence of these transformations, including route A: (1)→(2)→(3); route B: (1)→(3)→(2); and route C: (3)→(1)→(2). We investigated each of these three possible routes.

Route A: With this aim, we explored routes for the synthesis of the 5,10,15-triarylchlorin 11. Initially, we selected Fb-1a as the starting material (Scheme 6). A known procedure for the iodination of porphyrins (Shanmugathasan, S. et al., *J. Porphyrins Phthalocyanines* 2000, 4, 228–232; Wytko, J. et al., *Helv. Chim. Acta* 1998, 81, 1964–1977) was applied for the synthesis of the 15-iodo-substituted chlorin Fb-9. The reaction proceeded with high regioselectivity, affording Fb-9 in 58% yield. The high selectivity of this reaction is not surprising, as Woodward first reported the high reactivity toward electrophiles of the meso sites flanking the reduced ring (Woodward, R. B. et al., *J. Am. Chem. Soc.* 1961, 83, 4676–4678). Suzuki coupling of Fb-9 with 4,4,5,5-tetramethyl-2-phenyl-[1,3,2] dioxaborolane (10) (Nicolas, M. et al., *Eur. J. Org. Chem.* 2000, 1703–1710) gave Fb-11 in 79% yield along with the byproduct Pd-11 in 15% yield. This route affords straightforward access to trans-substituted chlorins.

A route to trans-substituted oxochlorins was examined by oxidation of the trans-substituted chlorins. Owing to the resistance of free base chlorins to oxidation on alumina, Fb-11 was converted to Zn-11. Application of the standard oxidation procedure (alumina/DDQ) to Zn-11 gave the corresponding hydroxychlorin HO-Zn-11 upon treatment with alumina, but the reaction with DDQ gave decomposition rather than the desired Oxo-Zn-11. Attempted oxidation of HO-Zn-11 with a wide variety of oxidizing

Scheme 5

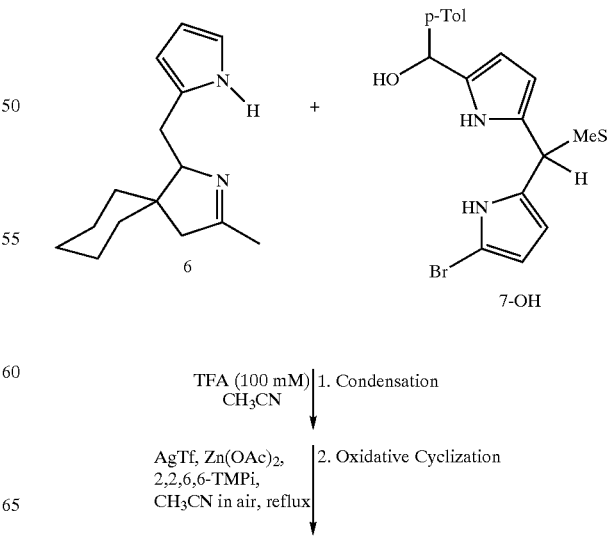

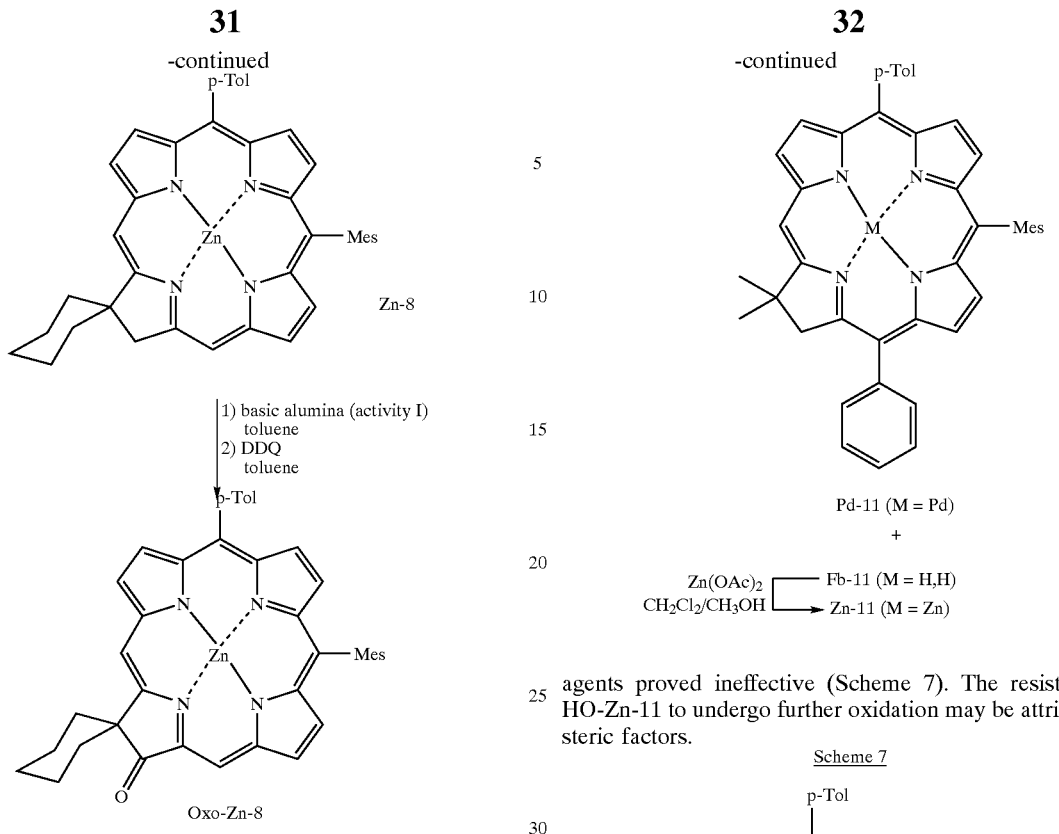
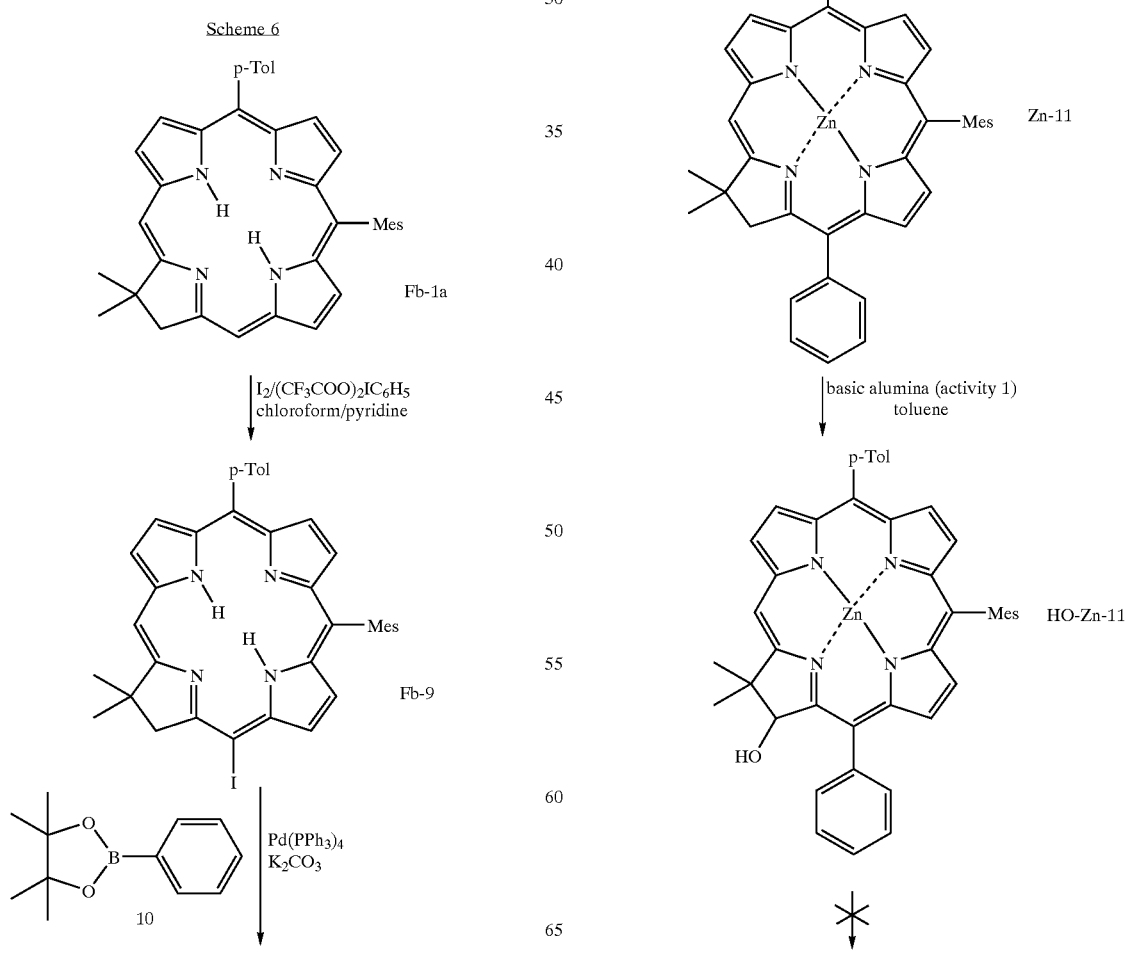
agents proved ineffective (Scheme 7). The resistance of HO-Zn-11 to undergo further oxidation may be attributed to steric factors.

Oxo-Zn-11

Route B: Subsequently, we examined oxidation of 15-halo-substituted Zn-chlorins (Scheme 8). The requisite 15-halo-substituted Zn-chlorins are readily available. Thus, the 15-iodo-substituted chlorin Zn-9 was obtained by zinc chelation of Fb-9, while the 15-bromo-substituted chlorin Zn-12 was obtained by selective bromination of Zn-1a upon reaction with N-bromosuccinimide. The corresponding hydroxychlorin HO-Zn-9 or HO-Zn-12 was obtained in a straightforward manner upon oxidation of Zn-9 or Zn-12 with alumina, respectively. (Note: together with HO-Zn-9, a trace amount of Oxo-Zn-9 was formed and characterized by UV-vis spectroscopy). However, the attempted oxidation with DDQ of the hydroxychlorin HO-Zn-9 or HO-Zn-12 gave no detectable oxochlorin, the same result obtained with HO-Zn-11. Thus, the hydroxychlorins with a 15-halo or phenyl substituent (HO-Zn-9, HO-Zn-11, and HO-Zn-12) are quite resistant toward oxidation required to form the oxochlorin.

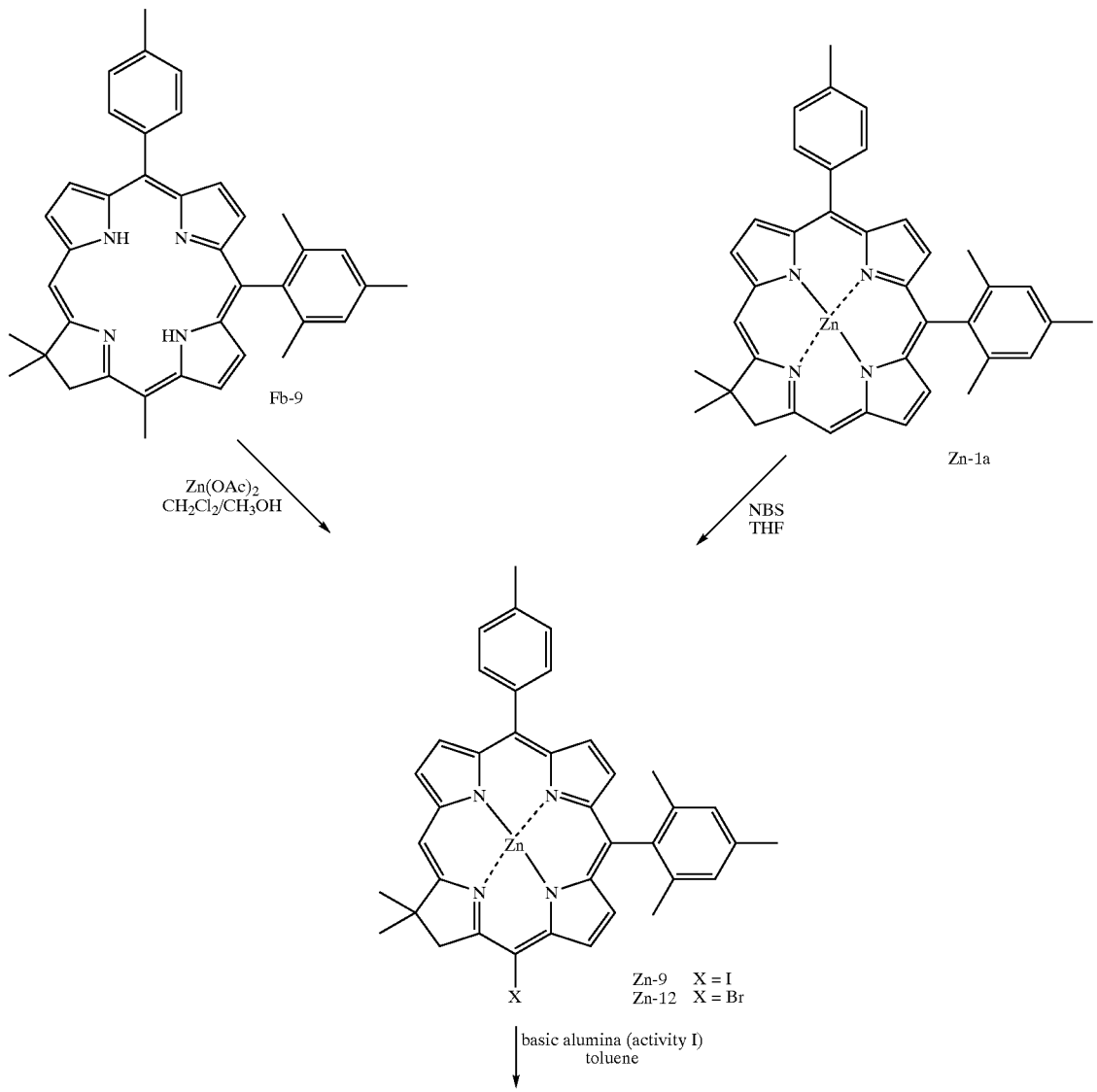

Scheme 8

-continued

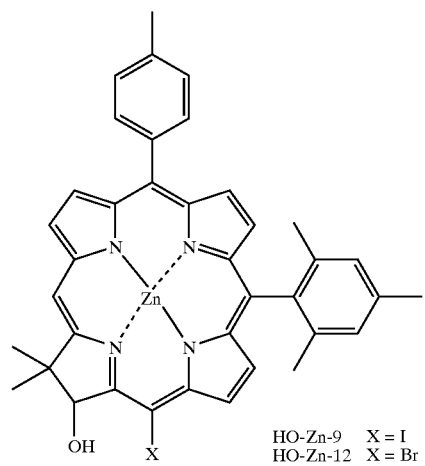

HO-Zn-9   X = I
HO-Zn-12  X = Br

DDQ
toluene

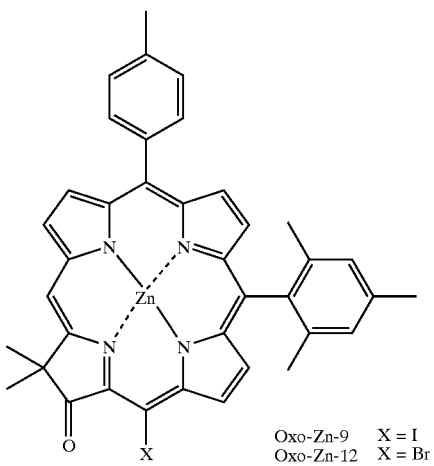

Oxo-Zn-9   X = I
Oxo-Zn-12  X = Br

Route C1: An alternate route to trans-substituted oxochlorins was examined by reversing the sequence of arylation/oxidation. Thus, iodination of Oxo-Fb-1a afforded the 15-iodochlorin Oxo-Fb-9, albeit in poor yield. Analysis of the reaction mixture indicated the presence of several iodinated components indicating the low selectivity of the iodination process. (A number of the side products arising through the iodination at 20- and β-pyrrole positions were separated and identified.) Suzuki coupling of Oxo-Fb-9 and 10 proceeded in high yield to give Oxo-Fb-11, which was metalated to give Oxo-Zn-11 (Scheme 9). This route enables the synthesis of a trans-substituted oxochlorin but the lack of selectivity in the iodination of the oxochlorin limits the efficiency of the overall synthesis.

Route C2: Treatment of the oxochlorin Oxo-Zn-1a with NBS gave the 20-bromo-substituted chlorin Oxo-Zn-13 in a quite selective manner (77% yield). This surprising result is entirely distinct from the result obtained upon iodination of Oxo-Fb-1a described above, whereupon the 15-iodo-substituted oxochlorin Oxo-Fb-9 was obtained along with a number of side products. The facile introduction of a halo substituent at the 20-position opens the door for a streamlined synthesis of trans-substituted oxochlorins. The Suzuki coupling of Oxo-Zn-13 and the dioxaborolane 10 gave the trans-substituted oxochlorin Oxo-Zn-14 (47%) together with the debrominated oxochlorin Oxo-Zn-1a (22%) (Scheme 10). This route toward the trans-substituted oxochlorin has two advantages compared to Route C1: (1) high selectivity, and (2) only three steps are required from the chlorin.

The various routes examined for preparing trans-substituted oxochlorins (5,15- or 10,20-substituted) are summarized in Table 1. The chemistry described herein provides routes to trans-substituted chlorins (5,15) and trans-substituted oxochlorins (5,15 or 10,20). The route to the 10,20-oxochlorins is considerably more efficient than that for preparing the 5,15-oxochlorins, due to the greater selectivity of 20-bromination of the zinc oxochlorin than 15-iodination of the free base oxochlorin. Regardless, both routes provide access to valuable oxochlorin building blocks that have heretofore been inaccessible.

TABLE 1

| | Comparison of Routes. | | | |
|---|---|---|---|---|
| Method | Reaction sequence[a] | Substrate for halogenation | trans-Substitution | Product |
| A | I/Ar/Ox | Fb-chlorin | — | none |
| B | I or Br/Ox/Ar | Fb-chlorin (I) Zn-chlorin (Br) | — | none |
| C1 | Ox/I/Ar | Fb-oxochlorin | 5,15 | Oxo-Fb-11 |
| C2 | Ox/Br/Ar | Zn-oxochlorin | 10,20 | Oxo-Zn-14 |

[a]The reaction sequences refer to iodination (I) or bromination (Br), arylation (Ar), and oxidation (Ox)

Scheme 9

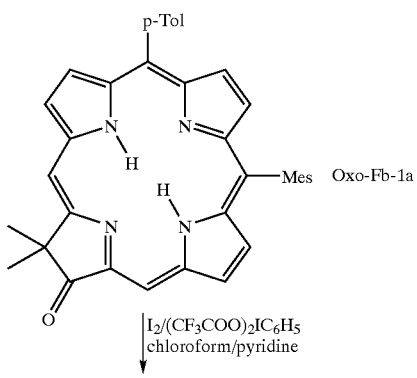

Oxo-Fb-1a

I₂/(CF₃COO)₂IC₆H₅
chloroform/pyridine

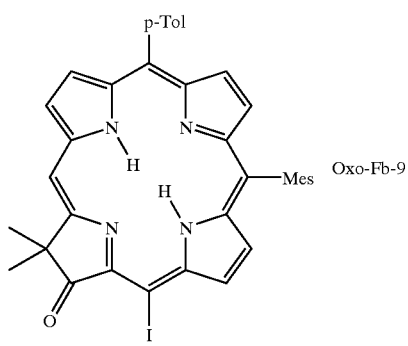

Oxo-Fb-9

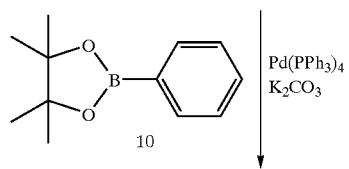

Pd(PPh₃)₄
K₂CO₃

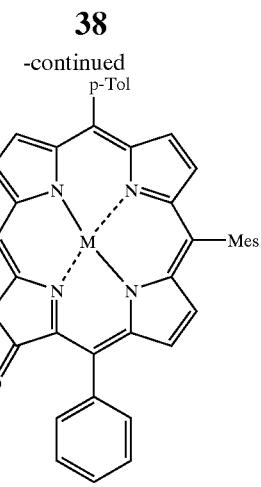

Zn(OAc)₂  ⎡ Oxo-Fb-11 (M = H, H)
CH₂Cl₂/CH₃OH  ⎣→ Oxo-Zn-11 (M = Zn)

Scheme 10

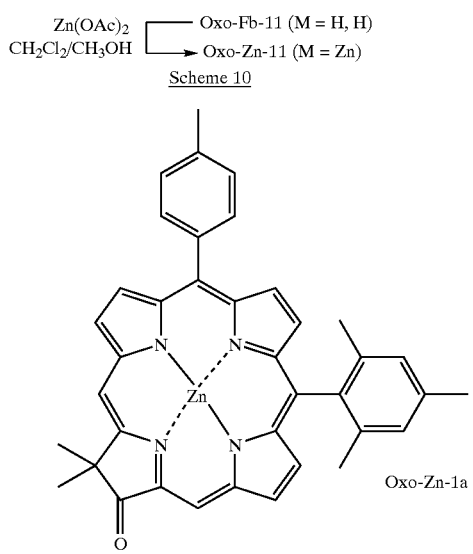

Oxo-Zn-1a

NBS / THF

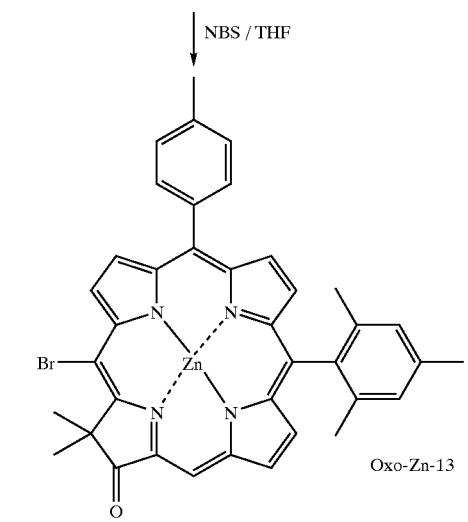

Oxo-Zn-13

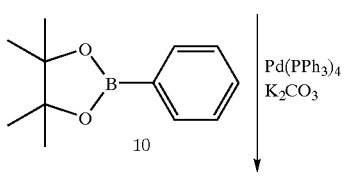

Pd(PPh₃)₄
K₂CO₃

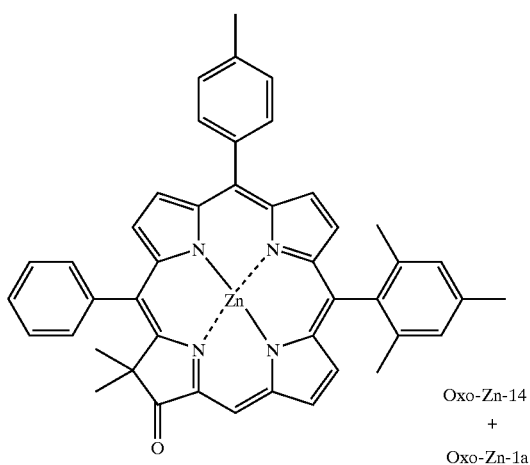

Oxo-Zn-14
+
Oxo-Zn-1a

EXAMPLE 3

Photophysical Studies of Oxochlorins

The absorption spectrum of oxochlorin Oxo-Zn-1a was collected in toluene at room temperature. The Soret band is red-shifted by 10 nm while the $Q_y(0,0)$ band is relatively unchanged from that of Zn-1a (FIG. 1). Similarly, Oxo-Fb-1a exhibits a Soret band which is sharper in comparison with that of Fb-1a. Similar features were observed for the other chlorin/oxochlorin species. Incorporation of an additional phenyl group at the 15-position does not appreciably change the absorption spectra of oxochlorins as evidenced by the slight (2–4 nm) shift observed for the Soret and the Q bands of Oxo-Fb-11 and Oxo-Zn-11 versus Oxo-Fb-1a and Oxo-Zn-1a, respectively. The long-wavelength absorption maxima for the chlorins are listed in Table 2.

TABLE 2[a]

| Compound | $Ar^1$ (5-position) | $Ar^2$ (10-position) | $R^f$ | $\gamma_{Qy(0,0)}$ (nm) | $\Phi_f$ |
|---|---|---|---|---|---|
| Zn-1a[b] | p-tolyl | mesityl | H | 608 | 0.065 |
| Zn-1b[b] | $C_6F_5$ | $C_6F_5$ | H | 608 | 0.072 |
| Zn-1c[c] | p-tolyl | e | H | 608 | 0.068 |
| Zn-1d[c] | 3,5-di-t-Bu-phenyl | 4-ethynylphenyl | H | 609 | 0.070 |
| Cu-1d | 3,5-di-t-Bu-phenyl | 4-ethynylphenyl | H | 604 | — |
| Zn-8[c] | p-tolyl | mesityl | H | 610 | — |
| Zn-11[c] | p-tolyl | mesityl | $C_6H_5$ | 613 | — |
| Fb-1a[b] | p-tolyl | mesityl | H | 641 | 0.29 |
| Fb-1b[b] | $C_6F_5$ | $C_6F_5$ | H | 644 | 0.26 |
| Fb-1c[d] | p-tolyl | e | H | 647 | 0.28 |
| Fb-1d[d] | 3,5-di-t-Bu-phenyl | 4-ethynylphenyl | H | 641 | 0.29 |
| Fb-11[d] | p-tolyl | mesityl | $C_6H_5$ | 645 | — |
| Oxo-Zn-1a[c] | p-tolyl | mesityl | H | 609 | 0.028 |
| Oxo-Zn-1b[c] | $C_6F_5$ | $C_6F_5$ | H | 613 | 0.024 |
| Oxo-Zn-1c[c] | p-tolyl | e | H | 610 | 0.030 |
| Oxo-Zn-1d[c] | 3,5-di-t-Bu-phenyl | 4-ethynylphenyl | H | 610 | 0.030 |
| Oxo-Cu-1d | 3,5-di-t-Bu-phenyl | 4-ethynylphenyl | H | 605 | |
| Oxo-Zn-8[c] | p-tolyl | mesityl | H | 611 | |
| Oxo-Zn-11[c] | p-tolyl | mesityl | $C_6H_5$ | 612 | 0.032 |
| Oxo-Zn-14 | p-tolyl | mesityl | $C_6H_5$ | 614 | 0.032 |
| Oxo-Fb-1a[d] | p-tolyl | mesityl | H | 643 | 0.064 |
| Oxo-Fb-1b[d] | $C_6F_5$ | $C_6F_5$ | H | 645 | 0.067 |
| Oxo-Fb-1c[d] | p-tolyl | e | H | 643 | 0.14 |
| Oxo-Fb-1d[d] | 3,5-di-t-Bu-phenyl | 4-ethynylphenyl | H | 643 | 0.14 |
| Oxo-Fb-11[d] | p-tolyl | mesityl | $C_6H_5$ | 646 | 0.086 |

[a]Spectral measurements were performed in toluene at room temperature with excitation in the Soret or Q-band region.
[b]Strachan J.-P. et al., J. Org. Chem. 2000.
[c]The fluorescence quantum yields were determined by ratioing to Zn-1a.
[d]The fluorescence quantum yields were determined by ratioing to Fb-1a.
[e]Substituent is 4-[2-(trimethylsilyl)ethoxycarbonyl]phenyl.
[f]Substituent at the 15-position.

The fluorescence emission spectra of the oxochlorins Oxo-Zn-1a-c show features similar to those of the parent chlorins Zn-1a-c (Table 2). In the case of Oxo-Zn-1a, the $\lambda_{Qy}(0,0)$ band, for example, appeared at 609 nm indicating negligible Stokes shift. Similarly, the $\lambda_{Qy}(0,0)$ band for Oxo-Zn-1b and Oxo-Zn-1c appeared at 614 and 610 nm, respectively, indicating a minimal Stokes shift. The fluorescence quantum yield ($\Phi_f$) of each oxochlorin Oxo-Zn-1a-d or Oxo-Zn-11 is similar to that of zinc(II)-meso-tetraphenylporphyrin (ZnTPP) (0.033). The free base oxochlorins have fluorescence quantum yields in the range of 0.06–0.14, which is comparable to that of meso-tetraphenylporphyrin (Fb-TPP) (0.11). In general, each oxochlorin examined has a $\Phi_f$ value that is approximately one-half to one-third that of the corresponding chlorin. Thus, the incorporation of the oxo functionality results in decreased emission efficiency. The lower fluorescence quantum yields of the oxochlorins do not diminish the utility of these pigments in light-harvesting systems. Indeed, ZnTPP and its derivatives have quite low fluorescence yields but are widely used to good effect in light-harvesting systems. The advantage of the oxochlorins versus porphyrins is the enhanced absorption in the red region of the spectrum.

EXAMPLE 4

Electrochemical Characterization of Oxochlorins

Figure 2:
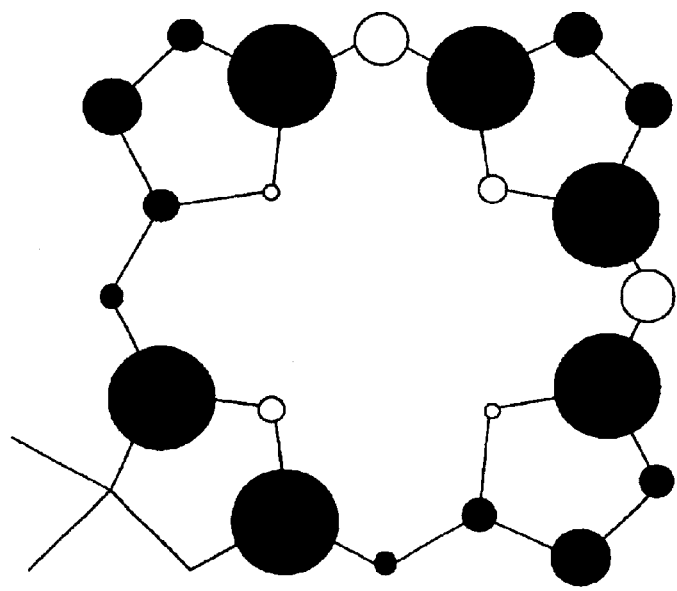
FIG. 2 shows the highest occupied molecular orbital of a chlorin ($a_2$ orbital). Note the very large electron density at the site adjacent to the methylene unit in the reduced ring.

The oxidation potentials of selected compounds such as Zn-1a,b and Oxo-Zn-1a,b were determined according to the procedure reported earlier (Yang, S. I. et al., *J. Porphyrins Phthalocyanines* 1999, 3, 117–147). The $E_{1/2}$ value for Zn-1a is 0.35 V whereas that for Oxo-Zn-1a is 0.59 V, which is comparable with the $E_{1/2}$ of ZnTPP (0.51 V; Yang, S. I. et al., *J. Porphyrins Phthalocyanines* 1999, 3, 117–147). Similarly, the $E_{1/2}$ value for Oxo-Zn-1b is 0.78 V, which is identical to that of zinc(II)-meso-tetrakis(2,6-difluorophenyl)porphyrin (0.78 V; Yang, S. I. et al., *J. Porphyrins Phthalocyanines* 1999, 3, 117–147). The $E_{1/2}$ value of Zn-1b is 0.55 V which is only slightly lower than that of ZnTPP. These results clearly indicate that a single oxo group imparts essentially the same electron-withdrawing effect on the chlorin as achieved with two meso-pentafluorophenyl groups. This is easily explainable on the basis of the electron density distribution in the HOMO of the chlorin indicating small orbital coefficients at the meso positions (FIG. 2) (Balasubramanian, T. et al., *J. Org. Chem.* 2000, 65, 7919–7929). The ability to substantially alter the electrochemical potential of the chlorins by introduction of a single oxo group in the reduced ring enables the meso and β-positions to be employed for synthetic handles and solubilizing groups. Thus, our strategy to incorporate an oxo group in the reduced ring is superior to the incorporation of electron-withdrawing substituents at the meso positions of the chlorin macrocycle. Thus, the advantage of oxochlorins versus chlorins is the greater resistance of the former versus the latter to oxidation.

EXAMPLE 5

Synthesis of Chlorin-Chlorin and Oxochlorin-Oxochlorin Dyads

The chlorin and oxochlorin dyads (other than $Zn_2$-Oxo-dyad) were synthesized by the Pd-mediated coupling of iodo-substituted and ethyne-substituted chlorin and oxochlorin building blocks (Scheme 11) (Wagner, R. W. et al., *Chem. Mater.* 1999, 11, 2974–2983). The progress of the reaction was monitored by analytical SEC. Each purified product was characterized by analytical SEC, LD-MS, UV-Vis spectroscopy, fluorescence spectroscopy (excluding $Cu_2$-dimers) and $^1$H NMR spectroscopy.

Scheme 11

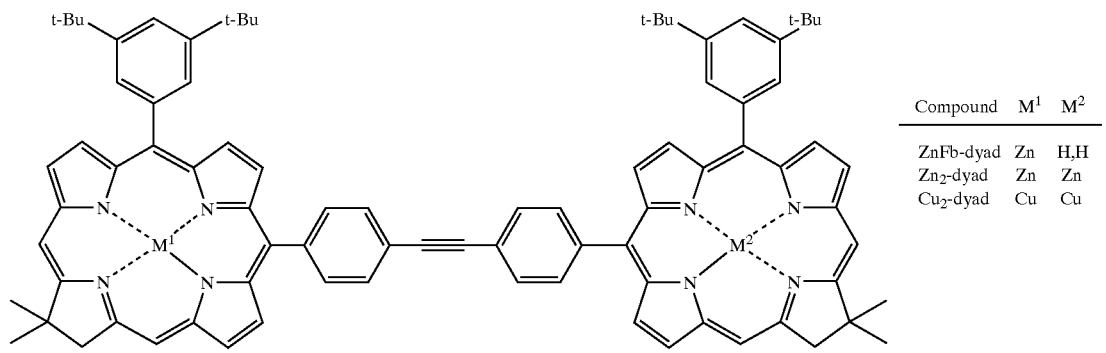

| Compound | M$^1$ | M$^2$ |
|---|---|---|
| ZnFb-dyad | Zn | H,H |
| Zn$_2$-dyad | Zn | Zn |
| Cu$_2$-dyad | Cu | Cu |

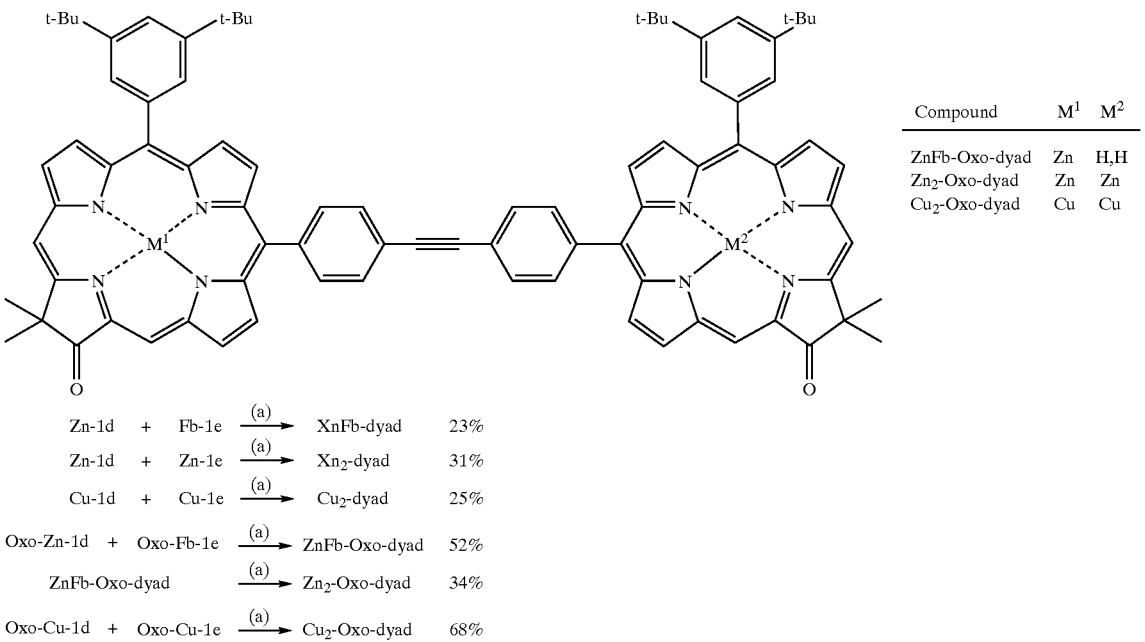

| Compound | M¹ | M² |
|---|---|---|
| ZnFb-Oxo-dyad | Zn | H,H |
| Zn$_2$-Oxo-dyad | Zn | Zn |
| Cu$_2$-Oxo-dyad | Cu | Cu |

| | | | | | |
|---|---|---|---|---|---|
| Zn-1d | + | Fb-1e | $\xrightarrow{(a)}$ | XnFb-dyad | 23% |
| Zn-1d | + | Zn-1e | $\xrightarrow{(a)}$ | Xn$_2$-dyad | 31% |
| Cu-1d | + | Cu-1e | $\xrightarrow{(a)}$ | Cu$_2$-dyad | 25% |
| Oxo-Zn-1d | + | Oxo-Fb-1e | $\xrightarrow{(a)}$ | ZnFb-Oxo-dyad | 52% |
| ZnFb-Oxo-dyad | | | $\xrightarrow{(a)}$ | Zn$_2$-Oxo-dyad | 34% |
| Oxo-Cu-1d | + | Oxo-Cu-1e | $\xrightarrow{(a)}$ | Cu$_2$-Oxo-dyad | 68% |

(a) Pd$_2$(dba)$_3$(0.15 eq), P$_{9o}$-tol)$_3$(1.2 eq), deaerated toluene-triethylamine (5:1)
(b) Zn(OAc)$_2$,CH$_2$Cl/methanol The coupling reaction of zinc chlorin Zn-1d and free base chlorin Fb-1e with Pd$_2$(dba)$_3$ and P(o-tol)$_3$ in toluene/triethylamine (5:1) at 35° C. afforded ZnFb-dyad. The Pd-mediated coupling was quite effective, as ZnFb-dyad was formed in >70% yield (by analytical SEC). The isolated yield was somewhat low (23%), because of the difficulties encountered during purification of the dyad which proved to be relatively insoluble in a variety of organic solvents. A similar sequence of reactions was employed to prepare Zn$_2$-dyad, Cu$_2$-dyad, ZnFb-Oxo-dyad, and Cu$_2$-Oxo-dyad. Zn$_2$-Oxo-dyad was prepared by treating ZnFb-Oxo-dyad with Zn(OAc)$_2$ in CH$_2$Cl$_2$/methanol (10:1) at room temperature.

EXAMPLE 6

Spectral and Photochemical Properties of Dyads

Figure 3:
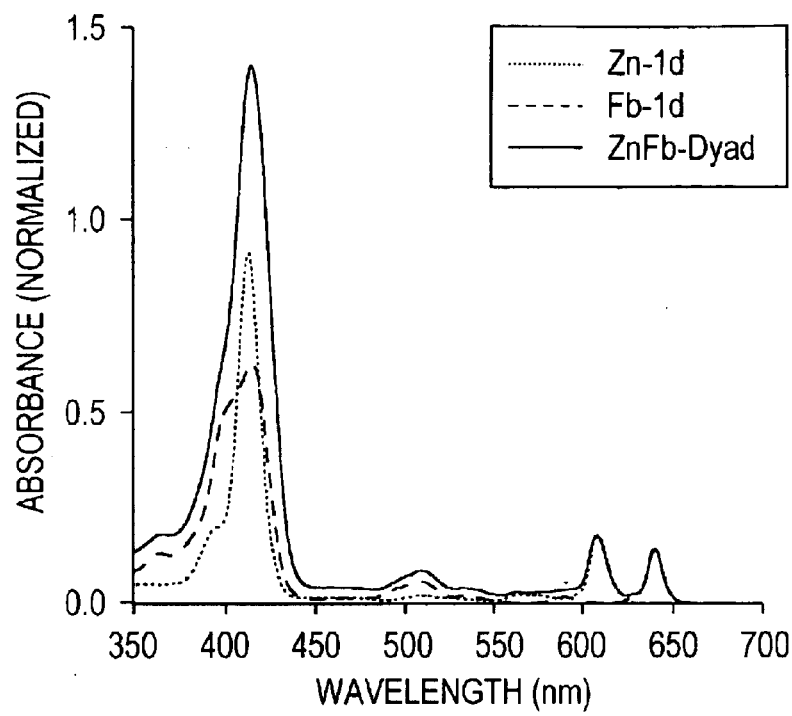
FIG. 3 illustrates the absorption spectra of the chlorin-chlorin dyad ZnFb-dyad and component parts in toluene at room temperature. The spectra of the Zn and Fb components have been normalized with that of the ZnFb-dyad at the respective long-wavelength Q bands.
Figure 4:
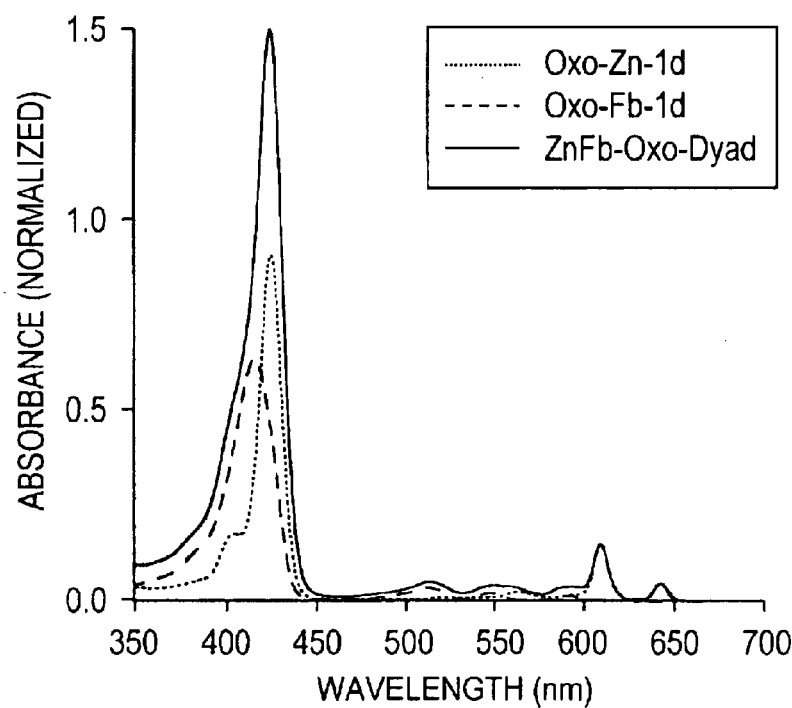
FIG. 4 illustrates the absorption spectra of the oxochlorin-oxochlorin dyad ZnFb-Oxo-dyad and component parts in toluene at room temperature. The spectra of the Zn and Fb components have been normalized with that of the ZnFb-Oxo-dyad at the respective long-wavelength Q bands.
Figure 5:
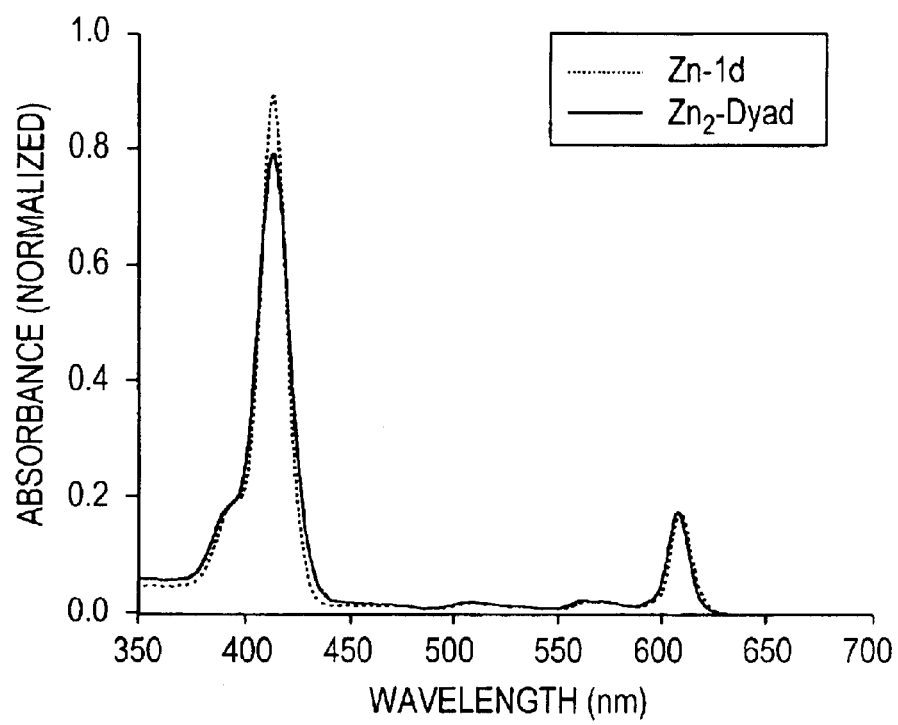
FIG. 5 illustrates the absorption spectra of the chlorin-chlorin dimer $Zn_2$-dyad and chlorin monomer in toluene at room temperature. The spectra have been normalized with that of the $Zn_2$-dyad at the long-wavelength Q band.
Figure 6:
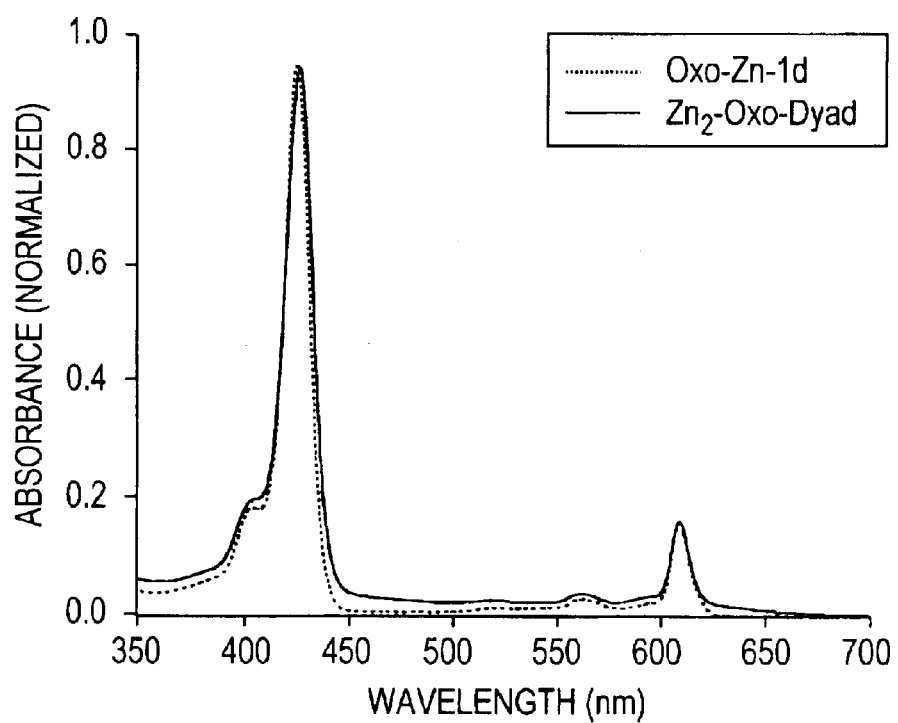
FIG. 6 illustrates the absorption spectra of the oxochlorin-oxochlorin dimer $Zn_2$-Oxo-dyad and oxochlorin monomer in toluene at room temperature. The spectra have been normalized with that of the $Zn_2$-Oxo-dyad at the long-wavelength Q band.

The absorption spectrum of each building block and dyad was measured in toluene at room temperature. The Q band region of ZnFb-dyad shows absorption at 609 and 641 mn, which is essentially the sum of the transitions of the representative monomers, Zn-1d and Fb-1d (FIG. 3). Similar features are observed for ZnFb-Oxo-dyad, which absorbs at 610 and 643 nm (FIG. 4). The all-zinc species Zn$_2$-dyad and Zn$_2$-Oxo-dyad give insignificant change of spectra compared to those of monomers Zn-1d and Oxo-Zn-1d (FIG. 5 and FIG. 6). In the case of the all-Cu-species Cu$_2$-dyad and Cu$_2$-Oxo-dyad, the Soret band is slightly red-shifted (2 nm) compared to that of the respective monomer Cu-1d or Oxo-Cu-id, while the Q-band is identical in each case.

Figure 7:
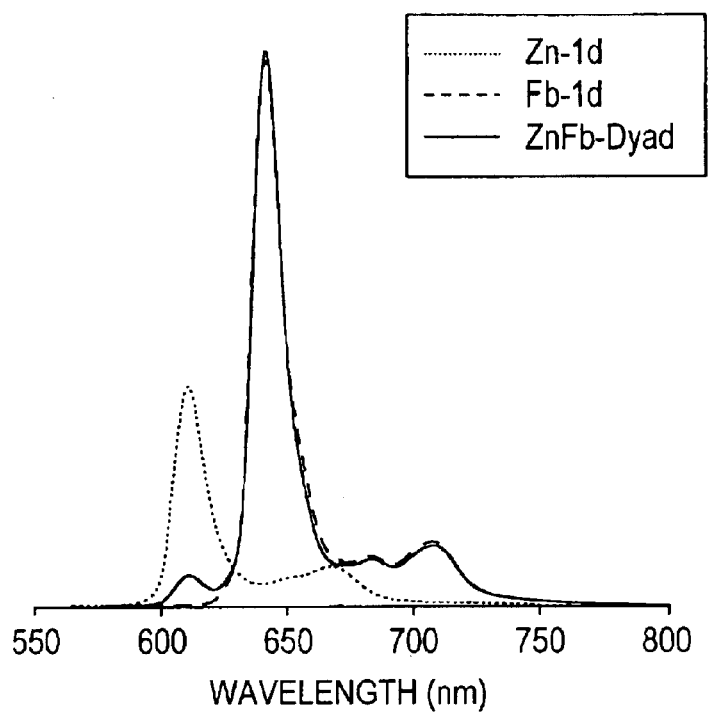
FIG. 7 illustrates the emission spectra of the chlorin-chlorin dyad ZnFb-dyad and component parts in toluene at room temperature ($\lambda_{ex}$ in Soret region). The spectra are shown at arbitrary intensities.
Figure 8:
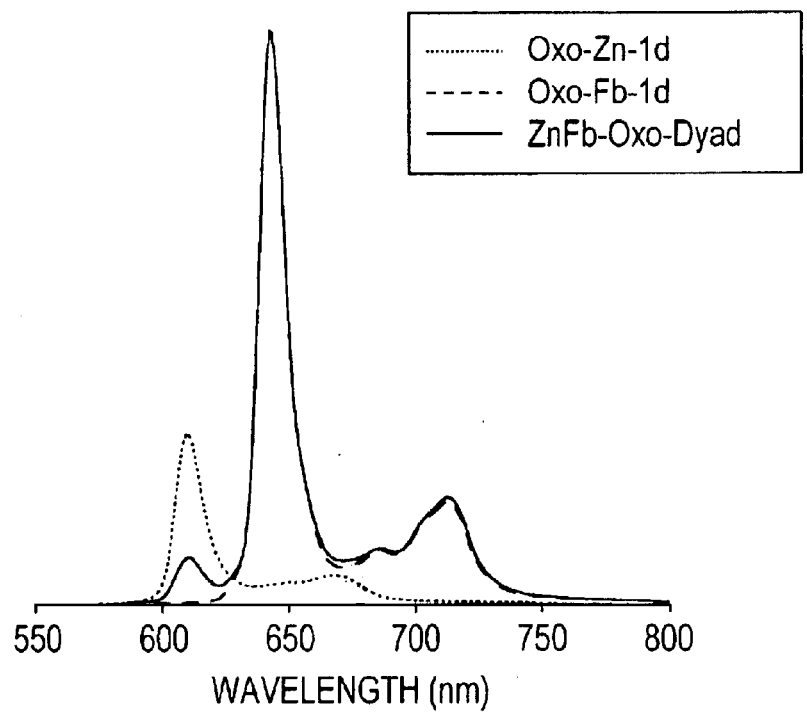
FIG. 8 shows the emission spectra of the oxochlorin-oxochlorin dyad ZnFb-Oxo-dyad and component parts in toluene at room temperature ($\lambda_{ex}$ in Soret region). The spectra are shown at arbitrary intensities.

In the steady state fluorescence spectroscopy, excitation of ZnFb-dyad at 415 mn results in characteristic bands at 611, 641, 683 and 708 mn, while the monomers show emission bands as follows; Zn-1d, 610 and 667 nm; Fb-1d, 641, 683 and 707 nm (FIG. 7). The intensity of the 611 nm in ZnFb-dyad decreased considerably in contrast to that of monomer Zn-1d. This is also the case with ZnFb-Oxo-dyad (FIG. 8). These results show that the excited Zn-chlorin or Zn-oxochlorin transfers energy to the Fb-chlorin or Fb-oxochlorin in the ZnFb dyads. The fluorescence spectrum of Zn$_2$-dyad or Zn$_2$-Oxo-dyad was identical to that of the corresponding Zn-monomer Zn-1d or Oxo-Zn-1d, respectively.

EXAMPLE 7

Förster Calculations

The rate of through-space (TS) energy transfer for each of the dyads was calculated using the program PhotochemCAD (Du, H. et al., *Photochem. Photobiol.* 1998, 68, 141–142). The results are shown in Table 3. The ZnFb-dyad and ZnFb-Oxo-dyad systems exhibit values for the spectral overlap term (J) comparable to that of the porphyrins as illustrated for the corresponding 4,4'-diphenylethyne-linked ZnFb-dyad comprised of porphyrins, ZnFbU (Hsiao, J.-S. et al., *J. Am. Chem. Soc.* 1996, 118, 11181–11193). However, the all-Zn-porphyrins exhibit a smaller J value (Zn$_2$U) while the Zn$_2$-chlorins and Zn$_2$-oxochlorins give J values that are roughly 10-times that for the ZnFb dyad case. Accordingly, the rate of TS energy transfer should be increased in the all-zinc arrays based on chlorins or oxochlorins but decreased in the all-zinc arrays based on porphyrins.

TABLE 3[a]

| Entry | Donor | Acceptor | $\xi_{Q(0,0)}$[g] | $\Phi_f$[h] | J (cm$^6$mmol$^{-1}$) | rel. J[i] | $\Phi_{TS}$[j] |
|---|---|---|---|---|---|---|---|
| 1[b] | Zn-1d | Fb-1d | 34 800 | 0.070 | 4.43 × 10$^{-14}$ | 1.4 | 90.7 |
| 2[b] | Zn-1d | Zn-1d | 46 900 | 0.070 | 2.66 × 10$^{-13}$ | 8.7 | 98.3 |
| 3[b] | Zn-Oxo-1d | Fb-Oxo-1d | 18 000 | 0.030 | 2.96 × 10$^{-14}$ | 0.97 | 73.5 |
| 4[b] | Zn-Oxo-1d | Zn-Oxo-1d | 54 000 | 0.030 | 3.05 × 10$^{-13}$ | 10. | 96.6 |
| 5[c,d] | ZuU[e] | FbU[f] |  | 0.035 | 3.06 × 10$^{-14}$ | 1.0 | 77.0 |
| 6[c] | ZnU[e] | ZnU[f] |  | 0.035 | 5.54 × 10$^{-15}$ | 0.18 | 37.8 |

[a]In all cases, the following parameters were employed: refractive index (n) = 1.490; actual distance (R) = 20.00 Å; orientation factor ($\kappa^2$) = 1.125 which assumes (1) that the transition dipole moment in each pigment is localized along the N—N axis bisecting the fully unsaturated pyrrole rings and (2) free rotation about the cylindrically symmetric ethyne axis.
[b]Integration was performed from 500–800 nm.
[c]Integration was performed from 570–700 nm.
[d]The previous Forster calculation (Hsiao, J.-S. et al., J. Am. Chem. Soc. 1996, 118, 11181–11193) for ZnFbU reported an average value for J based on four closely related ZnFb dyads.
[e]ZnU is zinc(II)-5,10,15-trimesityl-20-[4-(2-trimethylsilylethynyl)phenyl]porphyrin.
[f]FbU is 5,10,15-trimesityl-20-[4-(2-trimethylsilylethynyl)phenyl]porphyrin.
[g]The molar absorption coefficient of the long-wavelength absorption band, shown for the chlorin and oxochlorin species. In M$^{-1}$cm$^{-1}$.
[h]The $\Phi_f$ value refers to the donor in the absence of the acceptor.
[i]The relative J value is normalized to that for the porphyrin dyad ZnFbU for purposes of comparison.
[j]This term is the calculated energy-transfer efficiency based purely on the through-space mechanism.

In the arrays composed of porphyrins joined via the meso positions, the observed rate of energy transfer stems from the sum of through-bond (TB) and through-space (TS) mechanisms (Hsiao, J.-S. et al., J. Am. Chem. Soc. 1996, 118, 11181–11193). The dominant contributor in the porphyrins is the TB mechanism. The large contribution due to the TB mechanism is readily understandable based on consideration of the electron density in the frontier orbitals of the porphyrins. In particular, the porphyrin $a_{2u}$ orbital (HOMO) has significant electron density at the meso position, the site of attachment of the linker. In the chlorin systems, however, the HOMO has relatively little electron density at the meso position. Accordingly, it is expected that the dominant contributor to the observed energy-transfer process should be the TS mechanism. While studies of ZnFb systems have served as the benchmark for assessing energy transfer, the all-Zn-containing arrays are more desirable in light-harvesting systems. The Forster efficiencies calculated for the chlorins and oxochlorins are extremely encouraging in this regard. Whereas the Zn-porphyrins have poor overlap and, thus, poor TS interactions, the chlorins and oxochlorins have strongly enhanced interactions in the all-Zn-containing systems. Indeed, the J value for transfer between Zn-chlorins or transfer between Zn-oxochlorins is 50-times that for transfer between Zn-porphyrins. Thus, in the chlorins and oxochlorins, the all-Zn-containing systems should afford rapid rates of energy transfer.

The foregoing examples are illustrative of the present invention, and are not to be construed as limiting thereof. The invention is described by the following claims, with equivalents of the claims to be included therein.

What is claimed is:

1. A method of making an oxochlorin, comprising the steps of:
   oxidizing a chlorin to produce a mixture of hydroxychlorin and oxochlorin; and then
   oxidizing said hydroxychlorin in said mixture with 2,3-dichloro-5,6-dicyano-1,4-benzoquinone to produce a mixture consisting essentially of oxochlorin.

2. The method according to claim 1, wherein said step of oxidizing a chlorin is carried out by exposing said chlorin to alumina.

3. The method according to claim 1, wherein said step of oxidizing a chlorin is carried out in the presence of an oxidizing agent.

4. The method according to claim 3, wherein said oxidizing agent is oxygen or air.

5. The method according to claim 1, wherein said step of oxidizing a chlorin is carried out at a temperature of from 0 to 100° C.

6. The method according to claim 1, wherein said step of oxidizing a chlorin is carried out in an aromatic organic solvent.

7. The method according to claim 1, wherein said step of oxidizing a chlorin is carried out in toluene.

8. The method according to claim 1, wherein said step of oxidizing said hydroxychlorin is carried out at a temperature of from 0 to 100° C.

9. The method according to claim 1, wherein said step of oxidizing said hydroxychlorin is carried out in an aromatic organic solvent.

10. The method according to claim 1, wherein said step of oxidizing said hydroxychlorin is carried out in toluene.

11. The method according to claim 1, wherein said oxochlorin is a C-methylated chlorin.

12. The method according to claim 1, wherein said chlorin is metalated.

13. A method of making an oxochlorin, comprising the steps of:
   (a) providing a chlorin of Formula X:

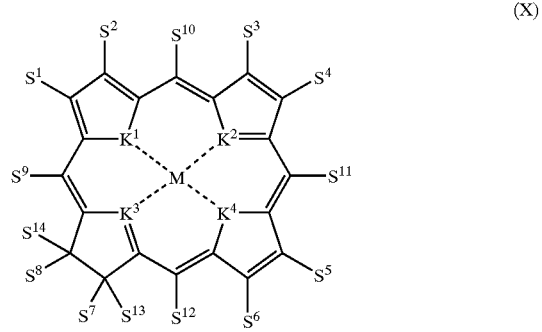

(X)

wherein:
- M is a metal selected from the group consisting of Zn, Mg, Pt, Pd, Sn and Al, or M is absent;
- $K^1$, $K^2$, $K^3$, and $K^4$ are hetero atoms independently selected from the group consisting of N, O, S, Se, Te, and CH;
- $S^1, S^2, S^3, S^4, S^5, S^6, S^7, S^8, S^9, S^{10}, S^{11}, S^{12}, S^{13}$, and $S^{14}$ are independently selected from the group consisting of H, aryl, phenyl, alkyl, cycloalkyl, spiroalkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
- and optionally either $S^1$ and $S^5$ are trans-substituted linking groups $Q^1$ and $Q^2$, $S^2$ and $S^6$ are trans-substituted linking groups $Q^1$ and $Q^2$, $S^{10}$ and $S^{12}$ are trans-substituted linking groups $Q^1$ and $Q^2$, or $S^9$ and $S^{11}$ are trans-substituted linking groups $Q^1$ and $Q^2$; and
- $Q^1$ and $Q^2$ are independently selected linking groups of the formula:

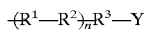

wherein:
- n is from 0 or 1 to 5 or 10;
- $R^3$ may be present or absent;
- $R^1$, $R^2$, and $R^3$ are each independently selected from the group consisting of ethene, ethyne, aryl, and heteroaryl groups, which aryl and heteroaryl groups may be unsubstituted or substituted one or more times with H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
- Y is a protected or unprotected reactive substituent selected from the group consisting of hydroxy, thio, seleno, telluro, ester, carboxylic acid, boronic acid, phenol, silane, sulfonic acid, phosphonic acid, alkylthiol, formyl, halo, alkenyl, alkynyl, haloalkyl, dialkyl phosphonate, alkyl sulfonate, alkyl carboxylate, acetylacetone, and dialkyl boronate groups;
- (b) oxidizing said chlorin to produce a mixture of hydroxychlorin and oxochlorin; and then
- (c) oxidizing said hydroxychlorin in said mixture with 2,3-dichloro-5,6-dicyano-1,4-benzoquinone in toluene to produce a mixture consisting essentially of oxochlorin, said oxochlorin comprising a compound of Formula X where $S^7$ and $S^{13}$ are together —O.

14. The method according to claim 13, wherein neither $S^8$ nor $S^{14}$ is H.

15. The method according to claim 13, wherein $S^9$ and $S^8$ are trans-substituted linking groups $Q^1$ and $Q^2$.

16. The method according to claim 13, wherein $S^{10}$ and $S^{11}$ are trans-substituted linking groups $Q^1$ and $Q^2$.

17. The method according to claim 13, wherein M is present.

18. The method according to claim 13, wherein M is Zn or Mg.

19. The method according to claim 13, wherein M is absent.

20. The method according to claim 13, wherein $K^1$, $K^2$, $K^3$, and $K_4$ are independently selected from the group consisting of N, O, S, and CH.

21. The method according to claim 13, wherein $K^1$, $K^2$, $K^3$, and $K^4$ are all N.

22. The method according to claim 13, wherein $S^4, S^7, S^8, S^9, S^{10}, S^{11}, S^{12}, S^{13}$, and $S^{14}$ are all alkyl.

* * * * *

UNITED STATES PATENT AND TRADEMARK OFFICE
CERTIFICATE OF CORRECTION

PATENT NO. : 6,765,092 B2
DATED : July 20, 2004
INVENTOR(S) : Lindsey et al.

It is certified that error appears in the above-identified patent and that said Letters Patent is hereby corrected as shown below:

Column 2,
Line 56, should read -- due to the reaction of $OsO_4$ at different sites; (2) different --
Line 58, should read -- β-positions of the pyrrote ring that is attacked by $OsO_4$, in --

Column 11,
Line 11, should read -- 408 (log ε=5.21), 501 (3.70), 569 (3.81), 605 (4.43) nm. --

Column 15,
Line 64, should read -- 424, 611 μm; $λ_{em}$ 611, 651, 669 nm. --

Column 18,
Line 19, should read -- 700.2181 ($C_{44}H_{36}N_4Zn$); $λ_{abs}$ 425, 612 nm. --

Column 43,
Lines 20-21, should read --
$$Zn\text{-}1d + Fb\text{-}1e \xrightarrow{(a)} ZnFb\text{-}dyad \quad 23\%$$
$$Zn\text{-}1d + Zn\text{-}1e \xrightarrow{(a)} Zn_2\text{-}dyad \quad 31\%$$

Line 64, should read -- Oxo-Cu-1d, while the Q-band is identical in each case. --

Column 48,
Line 15, should read -- Formula X where $S^7$ and $S^{13}$ are together =O. --
Line 29, should read -- $K^3$, and $K^4$ are independently selected from the group --

Signed and Sealed this

Fourteenth Day of December, 2004

JON W. DUDAS
*Director of the United States Patent and Trademark Office*